(12) United States Patent
Deming et al.

(10) Patent No.: US 10,351,591 B2
(45) Date of Patent: Jul. 16, 2019

(54) POLYPEPTIDES, PEPTIDES, AND PROTEINS FUNCTIONALIZED BY ALKYLATION OF THIOETHER GROUPS VIA RING-OPENING REACTIONS

(71) Applicant: The Regents of the University of California, Oakland, CA (US)

(72) Inventors: Timothy J. Deming, Los Angeles, CA (US); Eric G. Gharakhanian, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 88 days.

(21) Appl. No.: 15/559,981

(22) PCT Filed: Mar. 21, 2016

(86) PCT No.: PCT/US2016/023428
§ 371 (c)(1),
(2) Date: Sep. 20, 2017

(87) PCT Pub. No.: WO2016/154120
PCT Pub. Date: Sep. 29, 2016

(65) Prior Publication Data
US 2018/0105553 A1    Apr. 19, 2018

Related U.S. Application Data

(60) Provisional application No. 62/136,405, filed on Mar. 20, 2015.

(51) Int. Cl.
| | | |
|---|---|---|
| *C07K 1/00* | (2006.01) | |
| *C07K 7/06* | (2006.01) | |
| *C08G 69/10* | (2006.01) | |
| *C08G 69/48* | (2006.01) | |
| *G01N 33/68* | (2006.01) | |

(52) U.S. Cl.
CPC ............... *C07K 1/006* (2013.01); *C07K 7/06* (2013.01); *C08G 69/10* (2013.01); *C08G 69/48* (2013.01); *G01N 33/68* (2013.01)

(58) Field of Classification Search
CPC ........ C08G 69/10; C08G 69/48; G01N 33/68; C07K 7/06; C07K 1/006
See application file for complete search history.

(56) References Cited

U.S. PATENT DOCUMENTS

| | | | |
|---|---|---|---|
| 4,165,332 A | 8/1979 | Beard et al. | |
| 5,599,903 A * | 2/1997 | Kauvar | A61K 38/06 530/331 |
| 7,132,475 B2 | 11/2006 | Hubbell et al. | |
| 9,718,921 B2 | 8/2017 | Deming et al. | |
| 2010/0222407 A1 | 9/2010 | Segura et al. | |
| 2011/0177508 A1 | 7/2011 | Bestor et al. | |
| 2011/0223217 A1 | 9/2011 | Dixon et al. | |
| 2014/0294932 A1 | 10/2014 | Kim et al. | |

FOREIGN PATENT DOCUMENTS

| | | | | |
|---|---|---|---|---|
| CN | 1049269240 A | 9/2015 | | |
| EP | 0226827 A2 | 7/1987 | | |
| WO | WO-96/40757 A2 | 12/1996 | | |
| WO | WO-2010/023670 A2 | 3/2010 | | |
| WO | WO-2013/148727 A1 | 10/2013 | | |
| WO | WO-2017021334 A1 | 2/2017 | | |
| WO | WO-2017189860 A1 * | 11/2017 | ............. | C07K 1/006 |

OTHER PUBLICATIONS

Gharakhanian, et al., "Chemoselective synthesis of functional homocysteine residues in polypeptides and peptides", Chem. Commun., 2016, 52, 5336, Published Mar. 17, 2016. (Year: 2016).*
International Search Report and Written Opinion for International Application No. PCT/EP2016/068232 dated Nov. 14, 2016.
Alferiev et al., "High reactivity of alkyl sulfides towards epoxides under conditions of collagen fixation—a convenient approach to 2-amino-4-butyrolactones," Biomaterials, 22: 2501-06 (2001).
Catalog page for 2 bromoethyl triflate from ABX, http://web.archive.org/web/20090706013707/http://abx.de/chemicals/6182.html, available online Jul. 2009.
Extended European Search Report issued by the European Patent Office, dated Jan. 28, 2016, in related Application No. EP 15306247.
Gharakhanian et al., "Versatile Synthesis of Stable, Functional Polypeptides via Reaction with Epoxides," Biomacromolecules, 16: 1802-1806 (2015).
Hanson et al., "Nonionic block copolypeptide micelles containing a hydrophobic rac-leucine core," Macromolecules, 43:6268-9 (2010).
Huang et al., "Biologically active polymersomes from amphiphilic glycopeptides," J Am Chem Soc, 134:119-22 (2011).
International Search Report and Written Opinion for International Application No. PCT/US2013/033938 dated Jul. 22, 2013.
International Search Report from corresponding International Application No. PCT/US2014/018763, dated Jun. 2, 2014.
International Search Report from corresponding International Application No. PCT/US2016/023428, dated Jun. 29, 2016.
Kaplowitz et al., "The importance and regulation of hepatic glutathione," Yale J Biol Med, 54:497-502 (1981).
Kramer et al., "Glycopolypeptide conformations in bioactive block copolymer assemblies influence their nanoscale morphology," Soft Matter, 9(12):3389-95 (2013).
Kramer et al., "Preparation of Multifunctional and Multireactive Polypeptides via Methionine Alkylation," Biomacromolecules, 13: 1719-23 (2012).

(Continued)

*Primary Examiner* — Christopher M Rodd
(74) *Attorney, Agent, or Firm* — Foley Hoag LLP; David P. Halstead; Janine S. Ladislaw

(57) ABSTRACT

Some embodiments of the invention involve methods for introduction of various functional groups onto polypeptides, peptides and proteins by alkylation of thioether (a.k.a. sulfide) groups by ring opening reactions, creating new compositions of matter that may be useful for medical therapeutic or diagnostic applications. The thioether groups may either be present in the polypeptides, or may be added to polypeptides by chemical modification, such as by alkylation of thiol (sulfhydryl) groups.

19 Claims, 12 Drawing Sheets

(56) References Cited

OTHER PUBLICATIONS

Kultyshev et al., "S-Alkylation and S-Amination of Methyl Thioethers—Derivative of closo-[B12H12]2-. Synthesis of a Boronated Phosphonate, gem-Bisposphonates, and Dodecaborane-ortho-carborane Oligomers," J Am Chem Soc, 124(11): 2614-2624 (2002).
Kyte et al., "Purification of peptides that contain methionine residues," Method Enzymol, 91: 367-377 (1983).
March, Jerry Advanced Organic Chemistry (1992) ISBN 0-471-60180-2, p. 294-298 and p. 352-354.
Pande et al., "Suppression of phase separation in solutions of bovine lambda IV-crestallin by polar modification of the sulfur-containing amino acids," PNAS, 88(11): 4916-4920 (1991).
Reid, et al., "Selective identification and quantitative analysis of methionine containing peptides by charge derivatization and tandem mass spectrometry," J Am Soc Mass Spectr, 16(7): 1131-1150 (2005).
Ribeiro et al., "Influence of the amino-acid sequence on the inverse temperature transition of elastin-like polymers," Biophys J, 97:312-20 (2009).
Stark et al., "Alkylation of the methionine residues of ribonuclease in 8M urea," J Biol Chem, 269(11): 3755-3761 (1964).
Storer et al., "Aracyl triflates for preparing fluorescent and UV absorbing derivatives of unreactive carboxylates, amines, and other reactive metabolites," Analytica Chimic Acta, 558: 319-325 (2006).
Supplementary European Search Report dated Sep. 16, 2016 from EP 14 75 7627.
Taichi et al., "Suppression of side reactions during final deprotection employing a strong acid in boc chemistry: regeneration of methionyl residues from their sulfonium salts," Int J Peptide Res Ther, 15(4): 247-253 (2009).
Teeuwen et al., "'Clickable' elastins: elastin-like polypeptides functionalized with azide or alkyne groups," Chem Comm, 4022-4 (2009).
Toennies et al., "Methionine Studies VII. Sulfonium Derivatives," Journal of the American Chemical Society, vol. 67, 1945, pp. 849-851.
Umemura et al., "Alkylation of several Nucleophiles with Alkylsulfonium Salts," Bull Chem Soc Japan, 63(9): 2593-2600 (1990).

\* cited by examiner $M^{EG}$ (8): R = CH(OH)CH$_2$(OCH$_2$CH$_2$)$_3$OCH$_3$
$M^{N3}$ (4): R = CH(OH)CH$_2$N$_3$
$M^{Me}$: R = H          $M^{Bn}$: R = C$_6$H$_5$

| Conditions | pH | Dealkylation (mol %) | | | |
| --- | --- | --- | --- | --- | --- |
| | | $M^{N3}$ | $M^{EG}$ | $M^{Me}$ | $M^{Bn}$ |
| Acetate Buffer | 5.0 | 0 | 0 | 0 | 5 |
| PBS | 7.4 | 0 | 0 | 0 | 5 |
| Borate Buffer | 9.0 | 3 | 2 | 0 | 10 |
| 2-Mercaptopyridine | 7.4 | 2 | 1 | 0 | 100 |

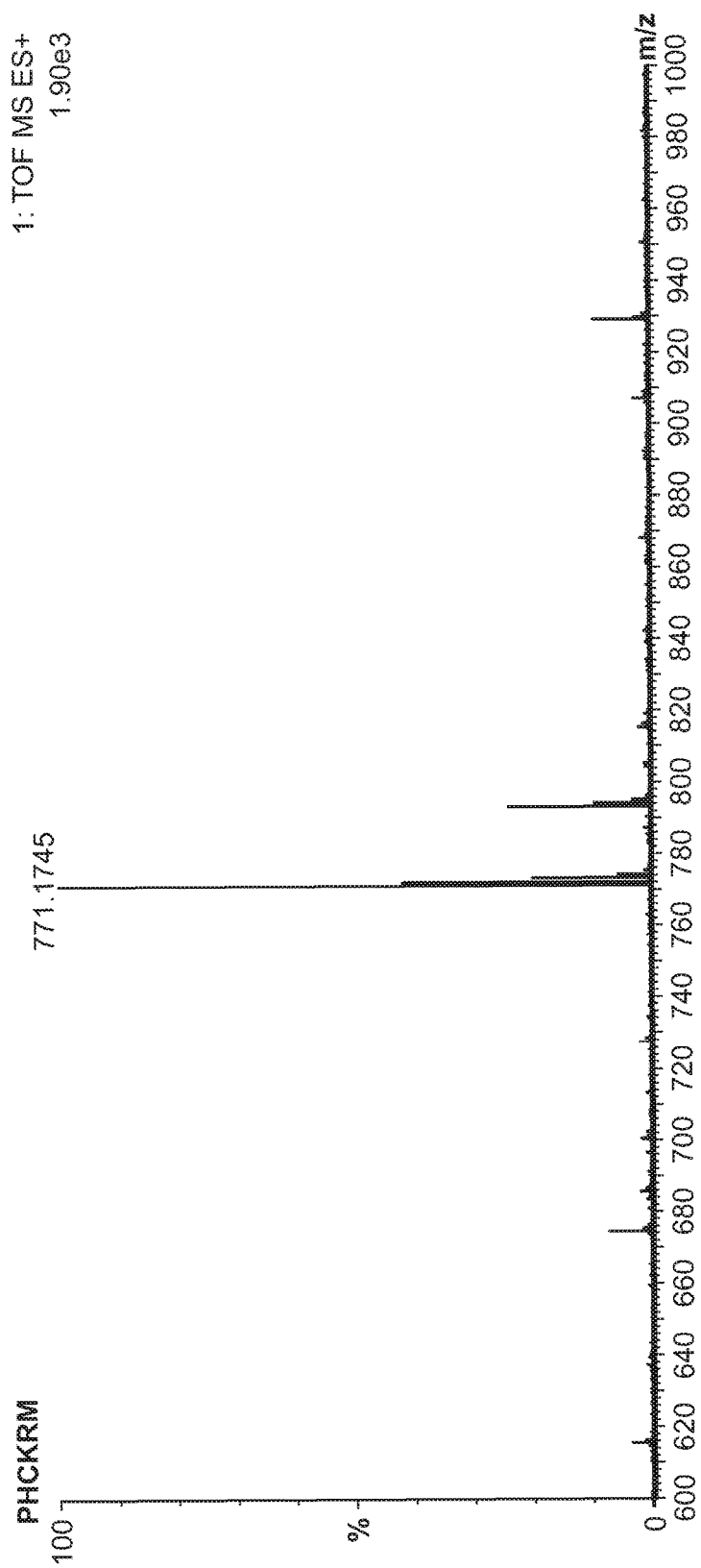

FIG. 6B (continued)

| Label | Amino Acid | Stereo-Isomer^x | R^1 | R^2 |
|---|---|---|---|---|
| a | Gly | — | H | H |
| b | Ala | L | H | Me |
| c | Val | L | Me | iPr |
| d | Val | L | H | iPr |
| e | Nle | rac | H | nBu |
| f | Leu | L | H | iBu |
| g | Phe | L | H | Bn |
| h | Phe | D | H | Bn |
| i | Phe | rac | H | Bn |
| j | Pgl | L | H | Ph | x = for marked (*) stereocenter.

POLYPEPTIDES, PEPTIDES, AND PROTEINS FUNCTIONALIZED BY ALKYLATION OF THIOETHER GROUPS VIA RING-OPENING REACTIONS

RELATED APPLICATIONS

This application is the U.S. National Stage Application of PCT/US2016/023428, filed Mar. 21, 2016, which claims the benefit of priority to United States Provisional Patent Application Ser. No. 62/136,405, filed Mar. 20, 2015, the contents of each of which are hereby incorporated by reference in their entireties.

GOVERNMENT SUPPORT

This invention was made with government support under Grant Numbers 1308081 and 1412367, awarded by the National Science Foundation. The government has certain rights in the invention.

BACKGROUND

The development of robust methods for facile synthesis of well-defined functional polymers is an ongoing challenge. To circumvent the common incompatibility of reactive side-chain functional groups with polymerization chemistries, there has been considerable effort to develop selective and efficient methods for post-polymerization modification. This is especially true for synthesis of functional polypeptides, which are desirable as mimics of post-translationally modified proteins and for uses in biological and medical applications. Consequently, a variety of precursor polypeptides, and their reactions with functional molecules, have been reported in recent years. Previous efforts have reported the reaction of methionine (Met) residues with alkylating agents as an efficient means to prepare functional polypeptides, which utilizes an inexpensive amino acid precursor and is broad in scope. In those systems, some functional groups can be installed using commercial reagents in water, while others require use of stoichiometric silver salts or preparation of reactive alkyl triflates and anhydrous conditions.

In addition, many of the activating groups in these examples (i.e. carbonyl, alkyne, aryl), also result in the product sulfonium ions that are unstable toward nucleophiles. These unstable sulfonium products often undergo dealkylation. While such reversibility is desirable for temporary modifications, the ability to prepare permanently functionalized materials under mild conditions is also important for many uses.

There exists a need for improved, efficient, general methods of introducing a wide range of functional groups onto polypeptides. Of specific interest are chemoselective reactions that exhibit high yields in protic solvents.

SUMMARY

In some embodiments, the invention relates to a compound of Formula I:

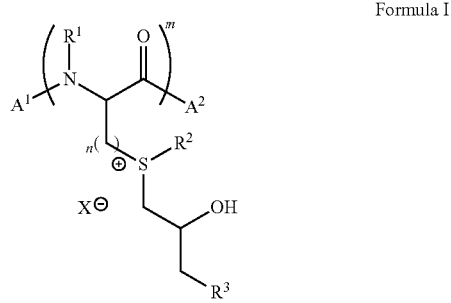

Formula I wherein, independently for each occurrence,
$R^1$ is H or alkyl;
$R^2$ is alkyl;
$R^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido;
m is 1-200, inclusive;
n is 1-4, inclusive;
$A^1$ is H, an amine protecting group, a natural or unnatural alpha amino acid, a peptide, an oligopeptide, a polypeptide, or a protein;
$A^2$ is OH, —O-(a carboxylate protecting group), a natural or unnatural alpha amino acid, a peptide, an oligopeptide, a polypeptide, or a protein; and
X is a monovalent anion.

In certain embodiments, the invention relates to any of the compounds described herein, wherein $R^3$ is -L-halo, -L-azide, -L-NHR$^1$, -L-NR$^1$-TFA, -L-NR$^1$—C(O)—O-alkyl, -L-NR$^1$—C(O)—CH$_2$—NR$^1$-TFA, -L-O—CH$_2$—CH=CH$_2$, -L-O—CH$_2$CCH, -L-O-alkyl, -L-O—C(O)-alkyl, -L-P(O)(O-alkyl)$_2$, -L-P(O)(OH)$_2$, -L-O—C(O)—C(halo)(alkyl)$_2$, -L-CH$_2$—P(O)(OH)$_2$, -L-O—CH$_2$CH—(C(O)NR$^1$-alkyl)(NR$^1$-TFA), -L-O—CH$_2$CH—(C(O)OR$^1$)(NR$^1$-TFA), -L-OCH$_2$—C(O)—OR$^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

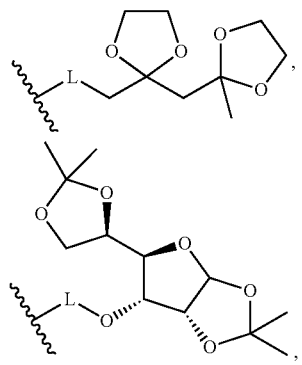

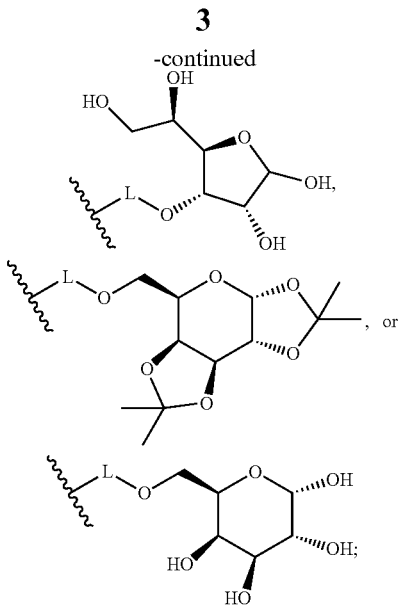

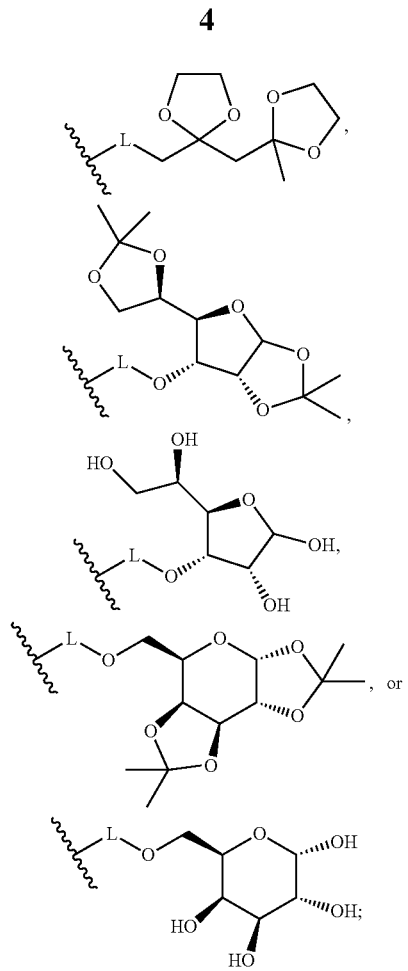

L is a bond or —(OCH$_2$CH$_2$)$_x$—, and x is 1-10.

In some embodiments, the invention relates to a peptide, an oligopeptide, a polypeptide, or a protein, wherein the peptide, oligopeptide, polypeptide, or protein comprises substructure I

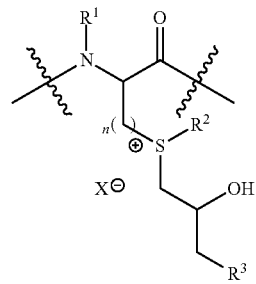

Substructure I wherein,

R$^1$ is H or alkyl;

R$^2$ is alkyl;

R$^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido;

n is 1-4, inclusive; and

X is a monovalent anion.

In certain embodiments, the invention relates to any of the peptides, oligopeptides, polypeptides, or proteins described herein, wherein R$^3$ is -L-halo, -L-azide, -L-NHR$^1$, -L-NR$^1$-TFA, -L-NR$^1$—C(O)—O-alkyl, -L-NR$^1$—C(O)—CH$_2$—NR$^1$-TFA, -L-O—CH$_2$—CH=CH$_2$, -L-CH$_2$CH$_2$CCH, -L-O-alkyl, -L-O—C(O)-alkyl, -L-P(O)(O-alkyl)$_2$, -L-P(O)(OH)$_2$, -L-O—C(O)—C(halo)(alkyl)$_2$, -L-CH$_2$—P(O)(O-alkyl)$_2$, -L-CH$_2$—P(O)(OH)$_2$, -L-O—CH$_2$CH—(C(O)NR$^1$-alkyl)(NR$^1$-TFA), -L-O—CH$_2$CH—(C(O)OR$^1$)(NR$^1$-TFA), -L-OCH$_2$—C(O)—OR$^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H, L is a bond or —(OCH$_2$CH$_2$)$_x$—, and x is 1-10.

In some embodiments, the invention relates to a process for chemically modifying a peptide, oligopeptide, polypeptide, or protein by alkylation of one or more thioether groups, comprising the steps of:

contacting a compound of formula II with an aqueous or polar organic solvent

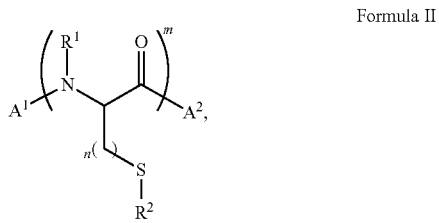

Formula II wherein, independently for each occurrence,

R$^1$ is H or alkyl;

R$^2$ is alkyl;

m is 1-200, inclusive;

n is 1-4, inclusive;

A$^1$ is H, an amine protecting group, a natural or unnatural alpha amino acid, a peptide, an oligopeptide, a polypeptide, or a protein;

A$^2$ is OH, —O-(a carboxylate protecting group), a natural or unnatural alpha amino acid, a peptide, an oligopeptide, a polypeptide, or a protein;

adding a compound of formula III

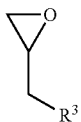

Formula III wherein, independently for each occurrence, $R^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido; and reacting the compound of formula II with the compound of formula III, thereby creating a compound of formula I

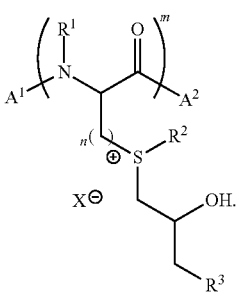

Formula I

In certain embodiments, the invention relates to any of the processes described herein, wherein $R^3$ is -L-halo, -L-azide, -L-NHR$^1$, -L-NR$^1$-TFA, -L-NR$^1$—C(O)—CH$_2$—NR$^1$-TFA, -L-O—CH$_2$—CH=CH$_2$, -L-O—CH$_2$CCH, -L-O-alkyl, -L-O—C(O)-alkyl, -L-P(O)(O-alkyl)$_2$, -L-P(O)(OH)$_2$, -L-O—C(O)—C(halo)(alkyl)$_2$, -L-CH$_2$—P(O)(O-alkyl)$_2$, -L-CH$_2$—P(O)(OH)$_2$, -L-O—CH$_2$CH—(C(O)NR$^1$-alkyl)(NR$^1$-TFA), -L-O—CH$_2$CH—(C(O)OR$^1$)(NR$^1$-TFA), -L-OCH$_2$—C(O)—OR$^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

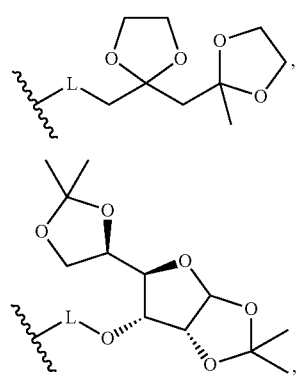

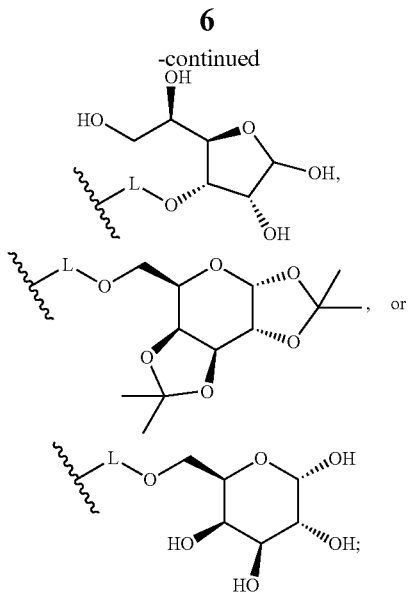

L is a bond or —(OCH$_2$CH$_2$)$_x$—, and x is 1-10.

In certain embodiments, the invention relates to compound formed by any of the processes described herein.

BRIEF DESCRIPTION OF THE FIGURES

FIG. 5A shows the full ESI-MS data for PHCKRM, with [M+H]$^+$ (771.1745 m/z) labeled.

DESCRIPTION

Overview

Figure 1:
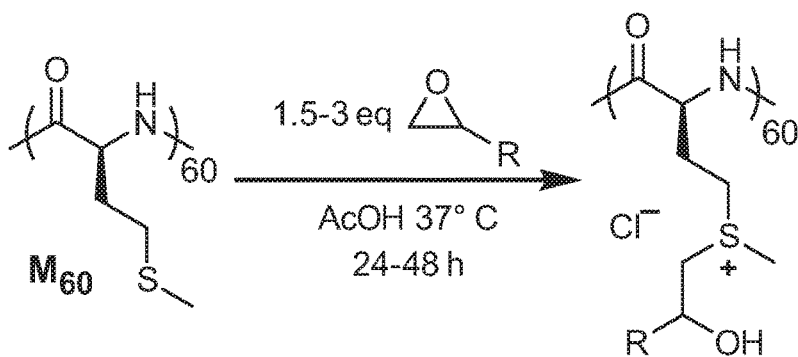
FIG. 1 depicts a schematic representation of the alkylation of M$_{60}$ with epoxides in acetic acid, 37° C. for 24-48 h followed by counterion exchange. Yield is total isolated yield of completely functionalized polypeptide, except for 9, 10, and 11. a=Percent modification for incomplete functionalizations are in parentheses.

In certain embodiments, the invention relates to a method of Met alkylation using epoxides - an efficient, general method to introduce a wide range of functional groups onto polypeptides. These functionalizations are notable since they can be conducted in wet protic media and are chemoselective, they utilize stable, easily accessible epoxide alkylating agents, and they allow facile incorporation of an unprecedented range of functional groups onto polypeptides using stable linkages.

Some embodiments of the invention involve methods for introduction of various functional groups onto polypeptides, peptides and proteins by alkylation of thioether (a.k.a. sulfide) groups by ring opening reactions, creating new compositions of matter that may be useful for medical therapeutic or diagnostic applications. The thioether groups may either be present in the polypeptides, or may be added to polypeptides by chemical modification, such as by alkylation of thiol (sulfhydryl) groups. These methods are general and can be applied to a wide range of different peptidic materials, including polypeptides, peptides and proteins. Certain embodiments of this invention relate to the modification of polypeptides via the thioether groups naturally present in methionine or in S-alkyl cysteine residues. A variety of new functionalities have been added to polypeptides via this process, including alkenes, alkynes, sulfonates, phosphonates, carbohydrates, amines, and alkyl halides, creating many new functional polypeptides, each of which are new compositions of matter. This alkylation process is a simple one-step modification and thus an economical way to prepare polypeptides with complex functionality that have potential use in applications including therapeutics, antimicrobials, delivery vehicles, coatings, composites, and scaffolds. The chemoselective nature of this reaction also makes it amenable for site-specific modification of peptides and proteins, highly desirable for therapeutic and diagnostic uses of these materials.

Embodiments of the technology described herein provide advantages over similar related technologies in the field. By way of example, some advantages include (but are not limited to) allowing formation of stable functional polypeptide products through use of more readily available cyclic alkylating agents (e.g., epoxides, aziridines, oxazolines, sultones). This allows the functionalization to be conducted in protic media, and avoids the need for use of stoichiometric silver salts or preparation of unstable alkyl triflates.

In some embodiments, the invention relates to the post-functionalization of poly(methionine) (poly(Met)). The functional groups introduced by the methods of the invention can be used to control polymer conformation. Numerous alkylating reagents have been found to react with poly(Met), allowing access to sulfonium derivatives functionalized with oligoethylene glycol (OEG), sugars, and other functional groups. These polymers display a range of tunable cloud points.

In addition, methodology has been developed for efficient alkylation of methionine residues using epoxides as a general strategy to introduce a wide range of functional groups onto polypeptides. Use of a spacer between epoxide and functional groups further allows addition of sterically demanding functionalities. Contrary to other methods to alkylate methionine residues, epoxide alkylations allow the reactions to be conducted in wet protic media and give sulfonium products that are stable against dealkylation. These functionalizations are notable since they are chemoselective, utilize stable and readily available epoxides, and allow facile incorporation of an unprecedented range of functional groups onto simple polypeptides using stable linkages.

For example, ethylene oxide (EO) reacts with many functional amino acids, including Met residues, to give stable β-hydroxyethyl sulfonium products (FIG. 1). Similar to reactions of alkyl halides with Met, the reaction of EO with proteins was observed to be selective for Met residues at pH<3, where all other nucleophilic functional groups are protonated and unreactive. Subsequent studies, utilizing N-protected Met amino acid, showed that substituted epoxides, such as propylene oxide and tert-butyl glycidyl ether, also react with Met to give sulfonium ions that are stable to acid and mild base. In these cases, the sulfur of Met adds primarily to the least hindered side of the epoxide to give the β-alkyl-β-hydroxyethyl sulfonium (FIG. 1). FIG. 1 shows alkylation of $M_{60}$ with epoxides in acetic acid, 37° C. for 24-48 h followed by counterion exchange. Yield is total isolated yield of completely functionalized polypeptide. a=Percent functionalization is reported instead of yield. These data show that addition of epoxides to Met residues is promising as a potentially chemoselective reaction to prepare stable sulfonium products, even in protic media. Since a large variety of epoxides are either commercially available or readily prepared, we sought to further develop this reaction as a general means to synthesize a broad range of functional and stable Met derivatives under mild conditions.

To test epoxide reactivity with polypeptides, we reacted a 60-mer Met polymer, $M_{60}$, with EO, propylene oxide or glycidyl azide under different conditions in protic media. It was observed that that highest degrees of functionalization and shortest reaction times were obtained using a small excess of epoxide (1.5 to 3 equivalents) in glacial AcOH at 37° C. (FIG. 1). The reaction is significantly faster under acidic conditions compared to neutral pH, although some epoxide is consumed by the acidic solvent, hence the use of 3 equivalents of epoxide per Met residue. If the epoxide is added over time (e.g., in stages), quantitative functionalization can also be obtained using 1.5 equivalents of epoxide. High degrees of functionalization were also obtained with epoxides containing other desirable functional groups, such as protected amine, alkyl chloride, alkene, alkyne, and oligoethyleneglycol (FIG. 1). Many of these are reactive groups that can be utilized for secondary functionalization using a diverse range of chemistries. The resulting sulfoniums were all highly water soluble and exclusively contained the alkyl substituents at the β-position except in the case of 2, which showed a trace of the α-alkylation product due to low steric demand of the substrate. Potential advantages of this methodology can be seen by the introduction of azido groups via an epoxide in wet media, which previously required use of an azido triflate in anhydrous solvent.

Figure 2:
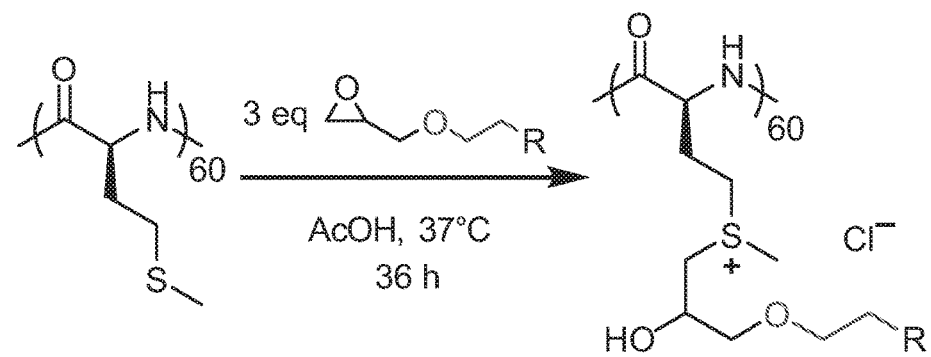
FIG. 2 depicts a schematic representation of the alkylation of M$_{60}$ with epoxides containing an oxoethylene spacer (red) in acetic acid, 37° C. for 36 h followed by ion exchange. Yield is total isolated yield of completely functionalized polypeptide. a=Sulfonate partially deprotected under reaction conditions. b=Yield is of fully deprotected glycopolypeptide.

Attempts to functionalize $M_{60}$ with more sterically demanding epoxides, including those containing monosaccharides, ATRP initiating groups, and phosphonates, demonstrated that that complete conversion of all Met residues to sulfoniums could not be readily obtained (FIG. 1). Such functional groups are difficult to introduce onto polypeptides by other methods, and are useful for a variety of applications including binding to biomolecules, synthesis of hybrid copolymers, or mimicking biomineralization processes. The inability to completely functionalize poly(Met) polymers with bulky epoxides was likely due to crowding of neighboring groups on the polymer backbone preventing further functionalization. To circumvent this issue, functional epoxides containing oxoethylene spacers that increased the distance between functional groups and the epoxides were prepared (FIG. 2). FIG. 2 shows alkylation of $M_{60}$ with epoxides containing an oxoethylene spacer (red) in acetic acid, 37° C. for 36 h followed by ion exchange. Yield is total isolated yield of completely functionalized polypeptide. a=Sulfonate partially deprotected under reaction conditions. b=Yield is of fully deprotected glycopolypeptide. With these longer tethers, quantitative alkylations of $M_{60}$ polymers with a wide array of large functional groups were achieved, allowing facile preparation of polypeptides containing a variety of unprecedented or difficult to introduce functional groups such as sulfonate, phosphonate, and malonate (FIG. 2). These polybetaines should possess interesting properties potentially useful for binding metal ions or creating non-fouling surfaces.

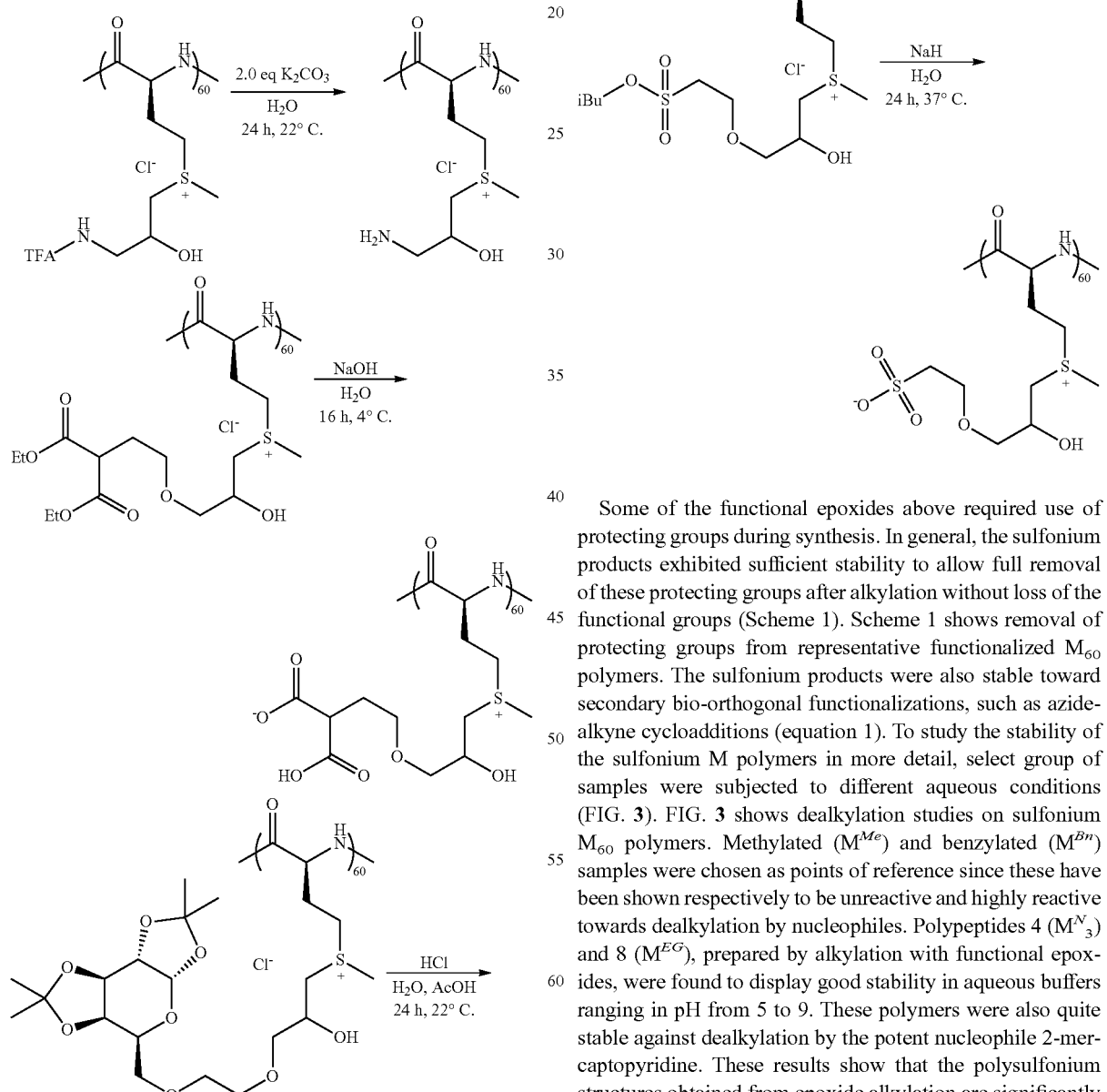

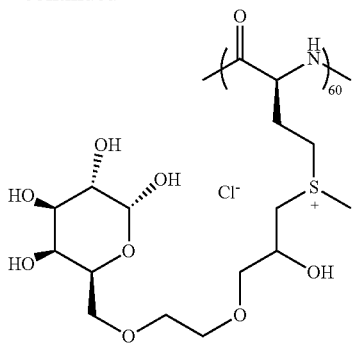

Figure 3:
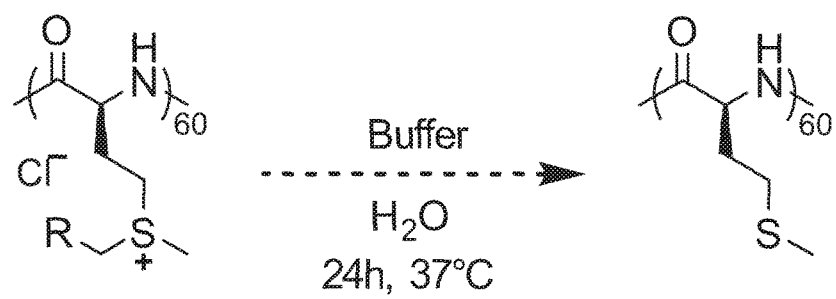
FIG. 3 depicts a schematic representation of dealkylation studies on sulfonium polymers.

Some of the functional epoxides above required use of protecting groups during synthesis. In general, the sulfonium products exhibited sufficient stability to allow full removal of these protecting groups after alkylation without loss of the functional groups (Scheme 1). Scheme 1 shows removal of protecting groups from representative functionalized $M_{60}$ polymers. The sulfonium products were also stable toward secondary bio-orthogonal functionalizations, such as azide-alkyne cycloadditions (equation 1). To study the stability of the sulfonium M polymers in more detail, select group of samples were subjected to different aqueous conditions (FIG. 3). FIG. 3 shows dealkylation studies on sulfonium $M_{60}$ polymers. Methylated ($M^{Me}$) and benzylated ($M^{Bn}$) samples were chosen as points of reference since these have been shown respectively to be unreactive and highly reactive towards dealkylation by nucleophiles. Polypeptides 4 ($M^{N}_{3}$) and 8 ($M^{EG}$), prepared by alkylation with functional epoxides, were found to display good stability in aqueous buffers ranging in pH from 5 to 9. These polymers were also quite stable against dealkylation by the potent nucleophile 2-mercaptopyridine. These results show that the polysulfonium structures obtained from epoxide alkylation are significantly more stable than those prepared from activated alkyl halides (e.g., benzyl bromide).

Equation 1

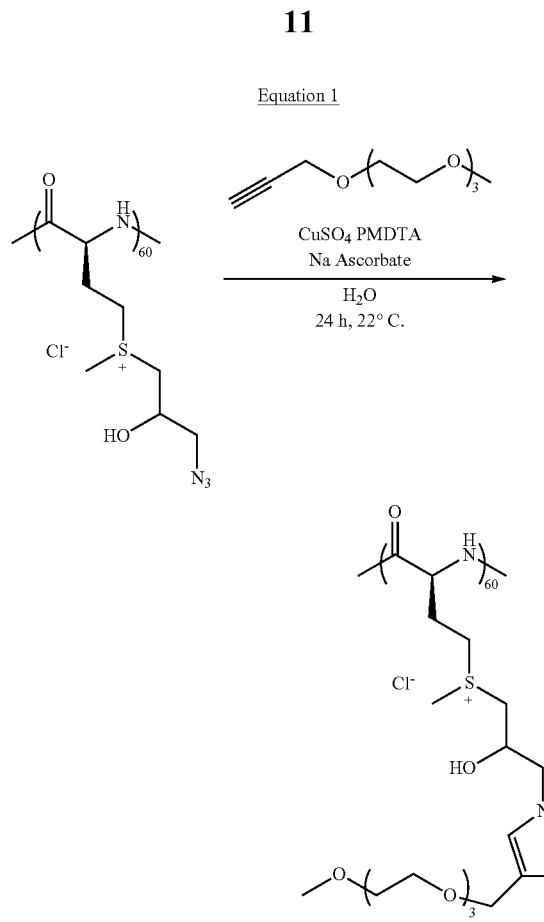

To test the chemoselectivity for epoxide alkylation of Met over other nucleophilic functional groups, a statistical copolymer of Met and L-lysine was prepared and its alkylation was studied. Lysine was selected as a competing nucleophile since it is the most abundant nucleophile found in proteins, it is more widely used in synthetic polypeptides compared to histidine or cysteine, and it is known to compete with thiol and imidazole groups in protein alkylations. Similar to results obtained in other Met alkylations, we found that the Met residues in the copolymer could be alkylated chemoselectively with glycidyl azide in acidic media in the presence of a fourfold excess of amine groups (equation 2).

Equation 2

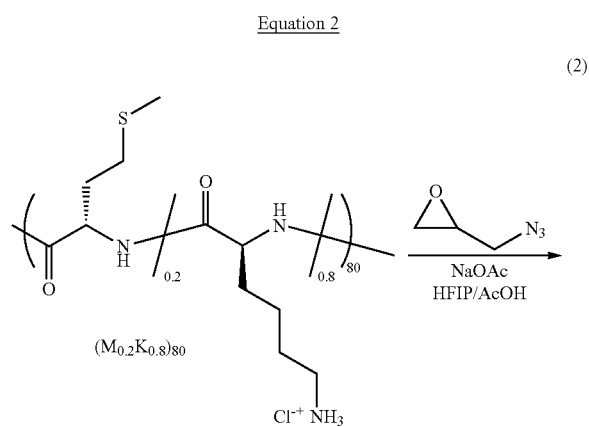

Figure 4A:
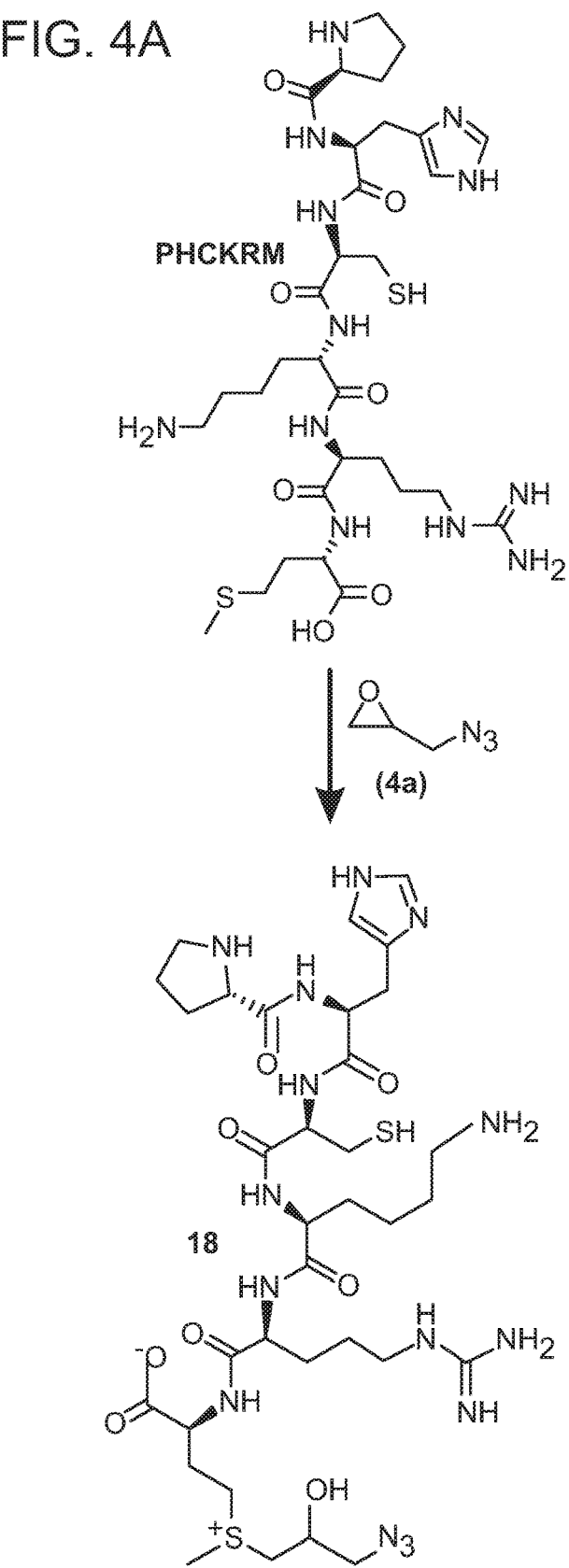
FIG. 4A shows a reaction scheme for alkylation of PHCKRM with glycidyl azide.
Figure 4B:
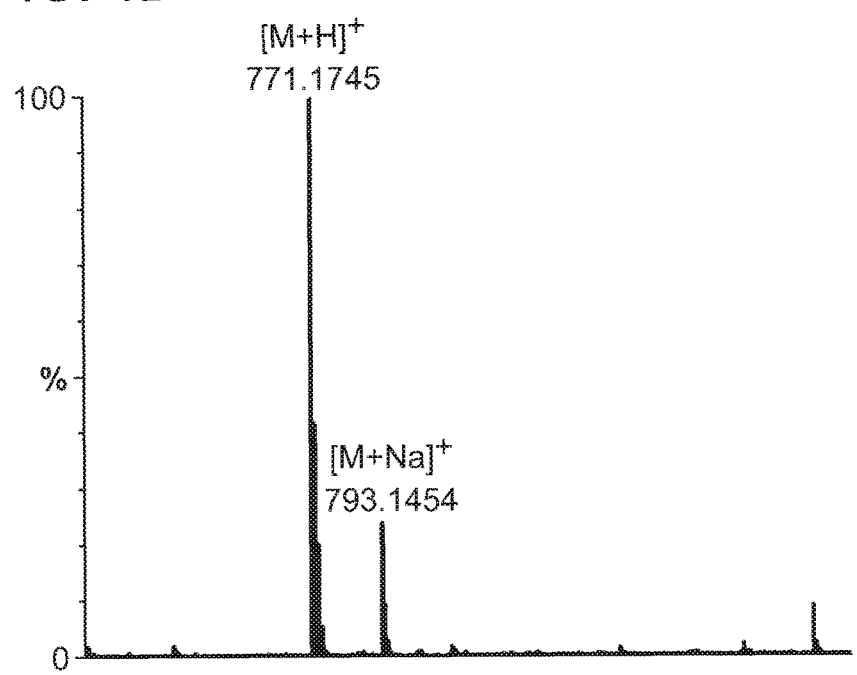
FIG. 4B shows a ESI-MS spectrum of PHCKRM with the [M+H]+ and [M+Na]+ peaks labeled.
Figure 4C:
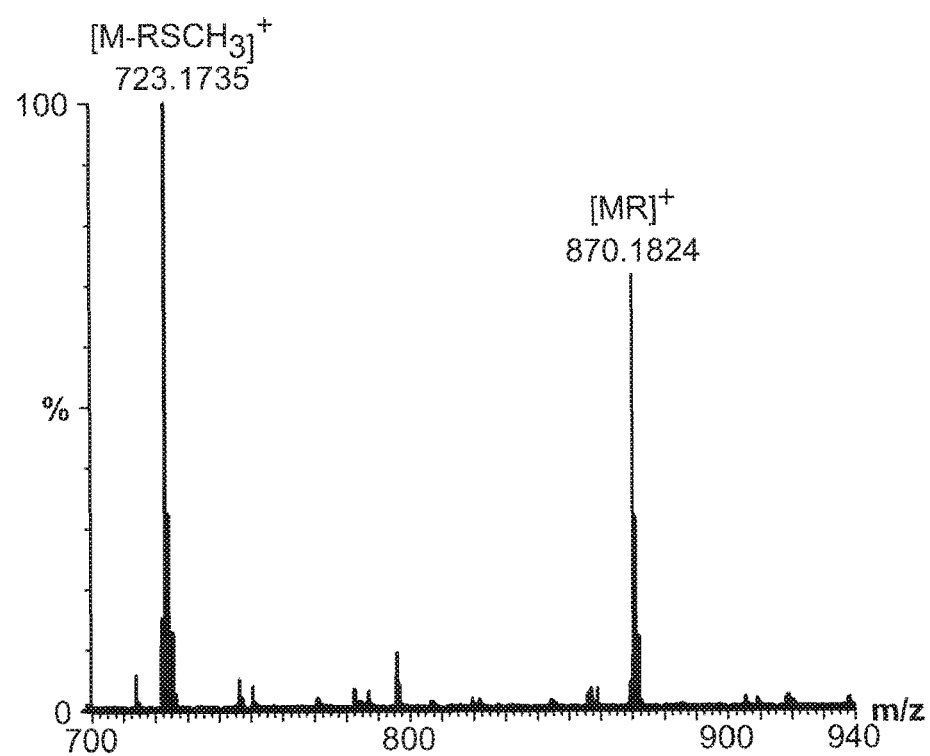
FIG. 4C shows a ESI-MS spectrum of the product after alkylation showing 18, [MR]+, as well as the characteristic [M-RSCH3]+ fragment.
Figure 5B:
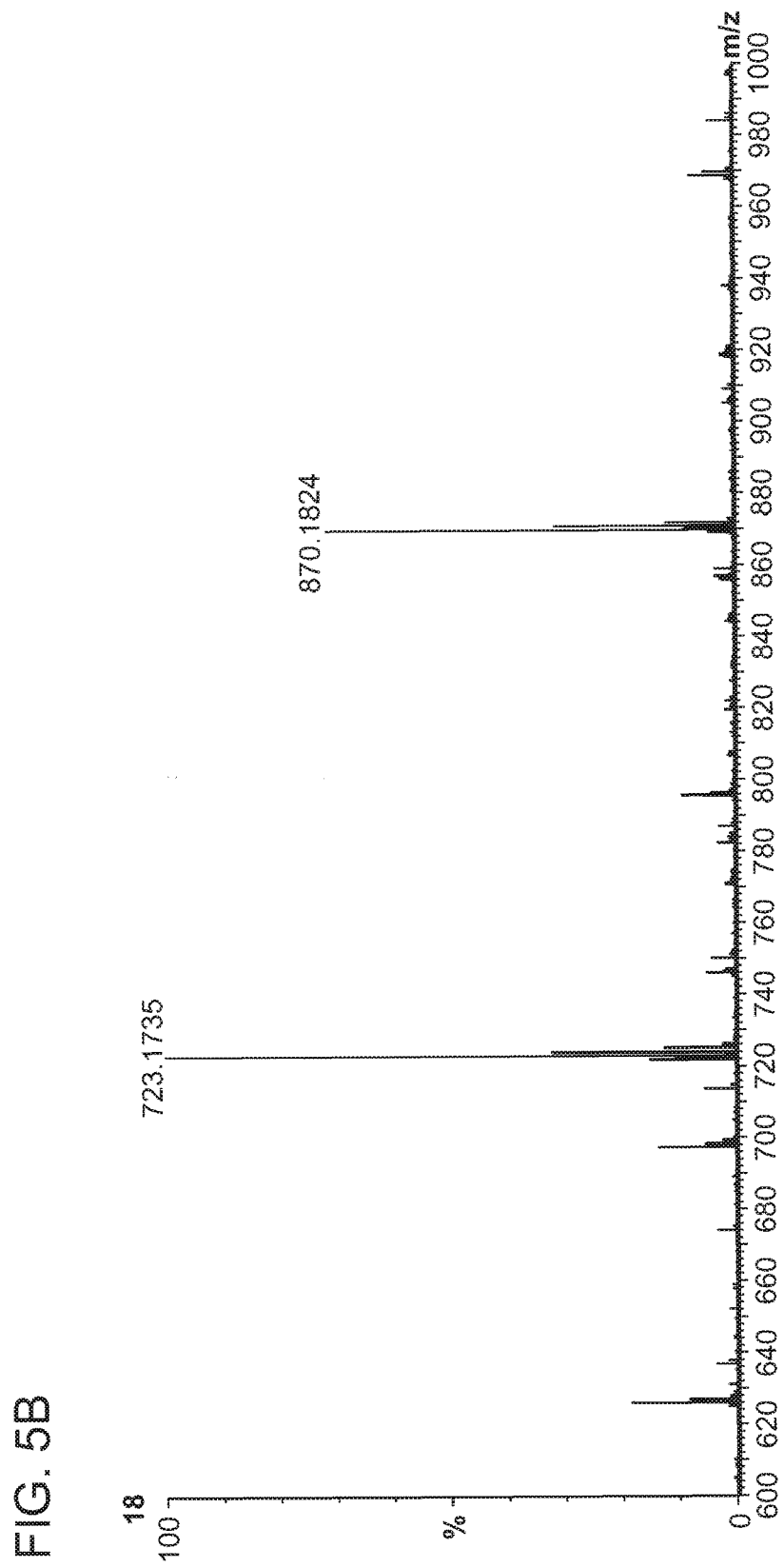
FIG. 5B shows the full ESI-MS data after alkylation of PHCKRM with glycidyl azide to give product 18 [MR]$^+$ and the characteristic [M-RSCH$_3$]$^+$ fragment, which are both labeled (870.1824& 723.1735 m/z, respectively).
Figures 6A, 6B:
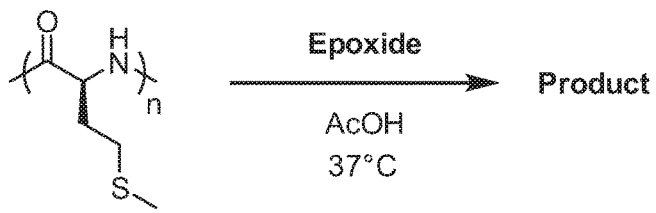
FIG. 6A depicts a schematic representation of an alkylation reaction of the invention.
FIG. 6B tabulates the structures of various compounds of the invention and epoxides used to synthesize them using the reaction from FIG. 6A.
Figure 6B:
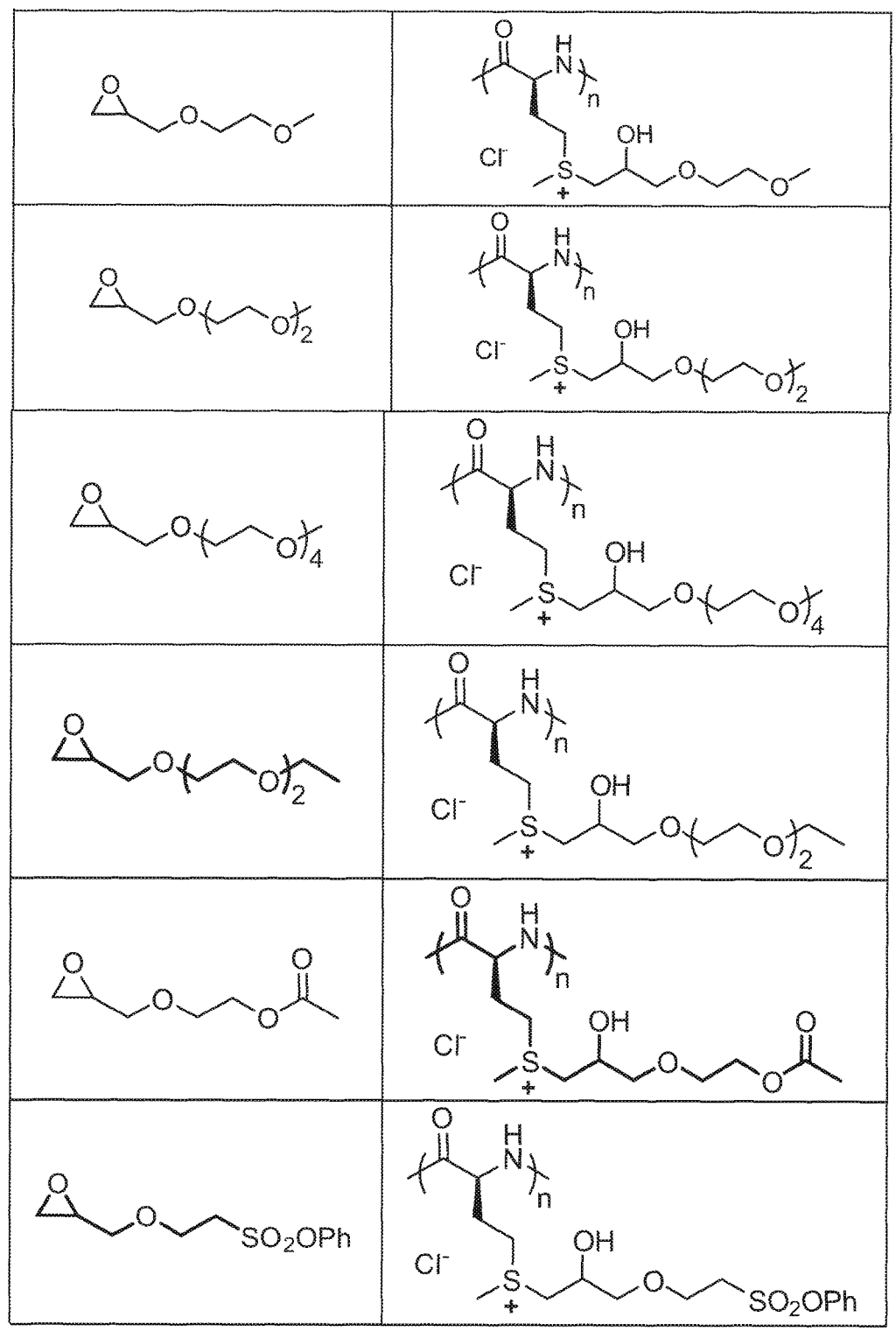
Figure 6B:
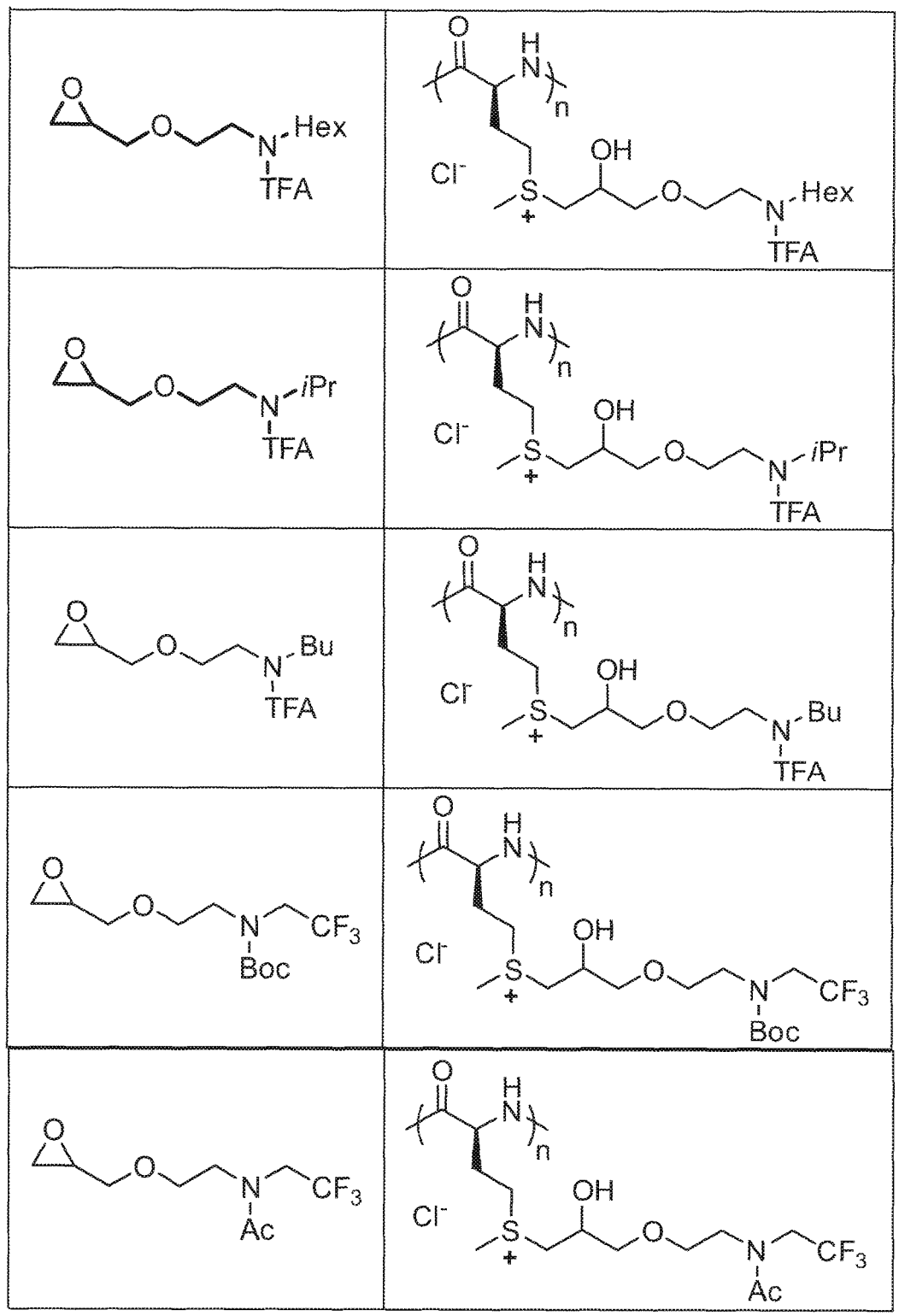
Figure 6B:
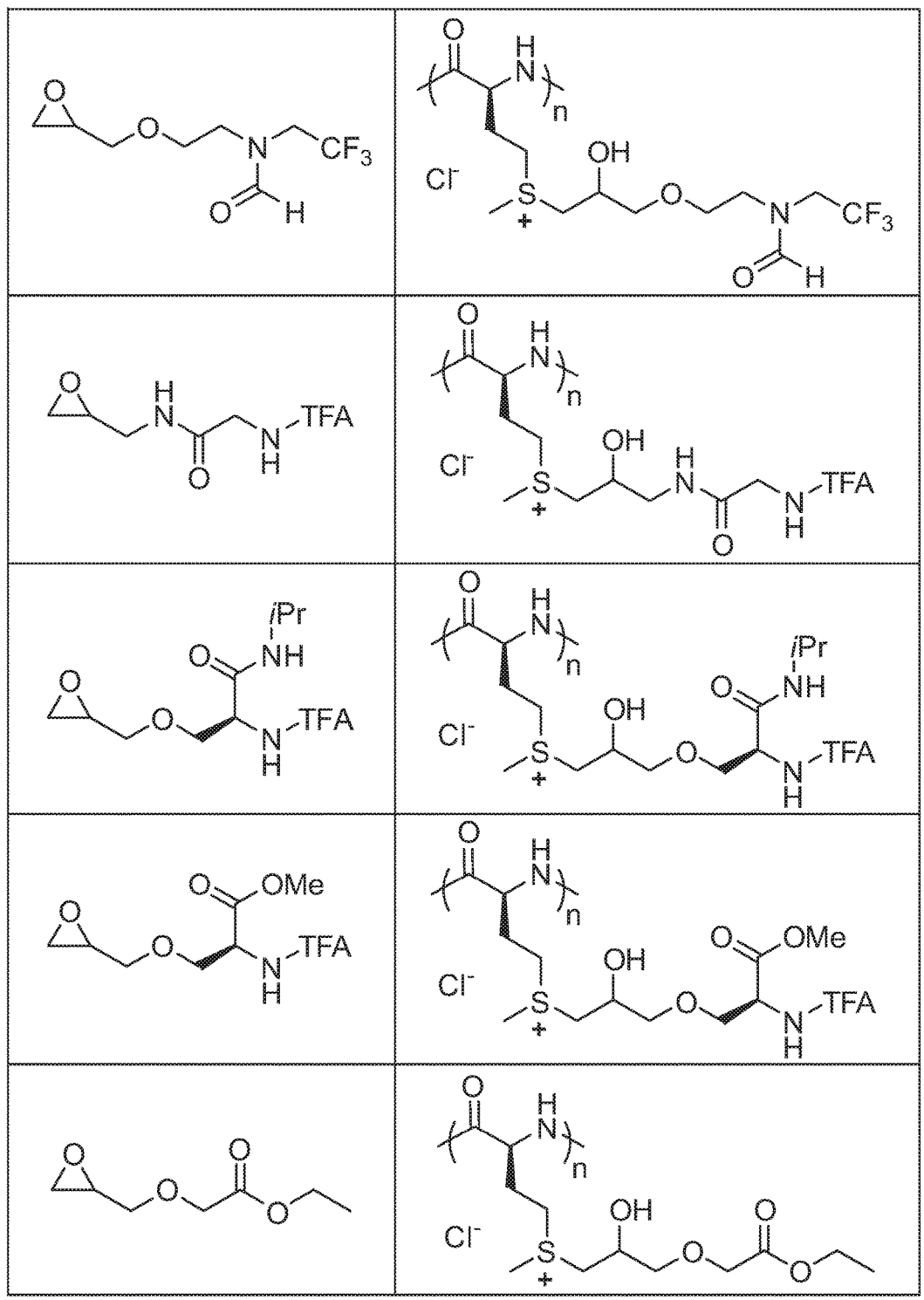

For a more demanding test of chemoselectivity, we attempted to alkylate only the Met residues in the antioxidant peptide PHCKRM, which also contains highly nucleophilic histidine, cysteine and lysine residues (FIG. 4). FIG. 4 shows chemoselective alkylation of PHCKRM. FIG. 4A shows the reaction scheme for alkylation of PHCKRM with glycidyl azide. FIG. 4B shows the ESI-MS spectrum of PHCKRM with the [M+H]$^+$ and [M+Na]$^+$ peaks labeled. FIG. 4C shows the product after alkylation showing 18, [MR]$^+$, as well as the characteristic [M-RSCH3]$^+$ fragment. Treatment of PHCKRM with glycidyl azide in glacial AcOH gave high conversion to a single product (18), where only the Met residue was alkylated. The identity of 18 was determined using ESI-MS (FIGS. 4A, B, and C, and FIGS. 5A and B), where the parent ion (MR+, R=3-azido-2-hydroxypropyl group) showed addition of only a single 100 Da 3-azido-2-hydroxypropyl group to the peptide. FIG. 5A shows full ESI-MS data for PHCKRM, with [M+H]$^+$ (771.1745 m/z) labeled. FIG. 5B shows full ESI-MS data after alkylation of PHCKRM with glycidyl azide to give product 18 [MR]$^+$ and the characteristic [M-RSCH$_3$]$^+$ fragment, which are both labeled (870.1824 & 723.1735 m/z, respectively). The additional presence of a single dominant fragment corresponding to the loss of the thioether RSCH$_3$, which is commonly observed in MS analysis of Met sulfonium ions, confirmed that alkylation was only occurring at the Met residue. These results also demonstrate that, in addition to polypeptides, peptides can be chemoselectively modified in high yields at Met residues via epoxide alkylation at low pH.

The alkylation of Met residues in polypeptides using functional epoxides was developed to give high yields of fully functionalized Met sulfonium containing materials, which were found to possess high water solubility and good stability against dealkylation. The epoxide reagents were optimized to provide chemoselective functionalization of Met, even when multiple sterically demanding functional groups were added to polypeptides. The methods described in this sample embodiment provide a simple solution for preparation of a diverse array of functional polypeptides in wet conditions using readily available or easily prepared reagents. Since M polymers are readily prepared from an inexpensive amino acid without need of protecting groups, this provides an economical approach to functional polypeptides will allow their use in an expanded array of applications.

Exemplary Compounds

In certain embodiments, the invention relates to a compound of Formula I:

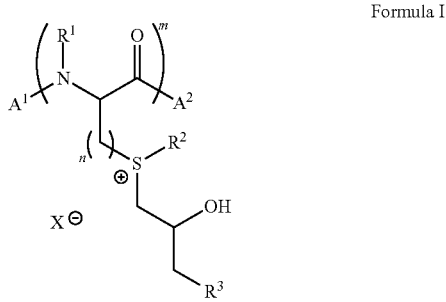

Formula I wherein, independently for each occurrence,
$R^1$ is H or alkyl;
$R^2$ is alkyl;
$R^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido;
m is 1-200, inclusive;
n is 1-4, inclusive;
$A^1$ is H, an amine protecting group, a natural or unnatural alpha amino acid, a peptide, an oligopeptide, a polypeptide, or a protein;
$A^2$ is OH, —O-(a carboxylate protecting group), a natural or unnatural alpha amino acid, a peptide, an oligopeptide, a polypeptide, or a protein; and
X is a monovalent anion.

In certain embodiments, the invention relates to any of the compounds described herein, wherein $R^1$ is preferably H.

In certain embodiments, the invention relates to any of the compounds described herein, wherein $R^1$ is alkyl, for example, methyl or ethyl.

In certain embodiments, the invention relates to any of the compounds described herein, wherein $R^2$ is methyl, ethyl, n-propyl, or n-butyl; preferably, $R^2$ is methyl.

In certain embodiments, the invention relates to any of the compounds described herein, wherein $R^3$ is substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido.

In certain embodiments, the invention relates to any of the compounds described herein, wherein $R^3$ is unsubstituted amino, unsubstituted alkyl, unsubstituted alkyloxy, azido, unsubstituted aryl, unsubstituted heteroaryl, halo, unsubstituted allyloxy, unsubstituted alkylcarbonyloxy, unsubstituted phosphonate, unsubstituted carbamate, or unsubstituted amido.

In certain embodiments, the invention relates to any of the compounds described herein, wherein $R^3$ is substituted amino, substituted alkyl, substituted alkyloxy, substituted aryl, substituted heteroaryl, substituted allyloxy, substituted alkylcarbonyloxy, substituted phosphonate, substituted carbamate, or substituted amido.

In certain embodiments, the invention relates to any of the compounds described herein, wherein $R^3$ is substituted alkyloxy, for example, heterocycloalkyloxy, phosphonate-substituted alkyloxy, acyloxyalkyloxy, aminoalkyloxy, aminoalkylamidoalkyloxy, or alkyloxycarbonylalkyloxy.

In certain embodiments, the invention relates to any of the compounds described herein, wherein $R^3$ is -L-halo, -L-azide, -L-NHR$^1$, -L-NR$^1$—C(O)—O-alkyl, -L-NR$^1$—C(O)—CH$_2$—NR$^1$-TFA, -L-O—CH$_2$—CH=CH$_2$, -L-O—CH$_2$CCH, -L-O-alkyl, -L-P(O)(O-alkyl)$_2$, -L-P(O)(OH)$_2$, -L-O—C(O)—C(halo)(alkyl)$_2$, -L-CH$_2$—P(O)(O-alkyl)$_2$, -L-CH$_2$—P(O)(OH)$_2$, -L-O—CH$_2$CH—(C(O)NR$^1$-alkyl)(NR$^1$-TFA), -L-O—CH$_2$CH—(C(O)OR$^1$)(NR$^1$-TFA), -L-OCH$_2$—C(O)—OR$^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

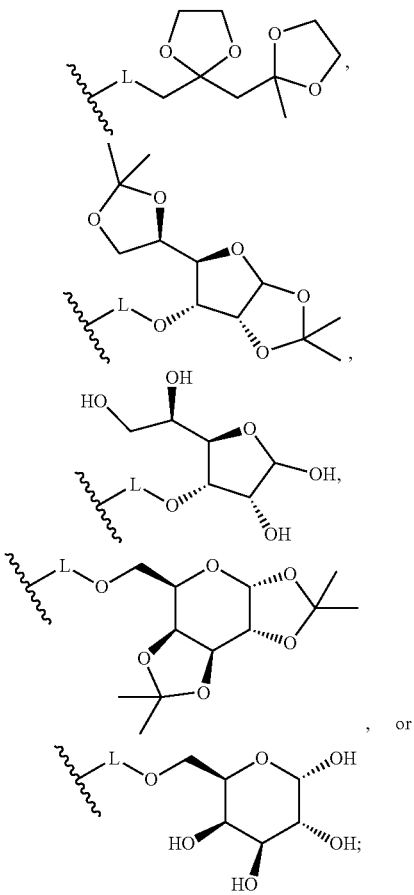

L is a bond or —(OCH$_2$CH$_2$)$_x$—, and x is 1-10.

In certain embodiments, the invention relates to any of the compounds described herein, wherein x is 1, 2, 3, 4, 5, or 6; preferably, x is 2, 3, or 4.

In certain embodiments, the invention relates to any of the compounds described herein, wherein m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, m is 1. In other embodiments, m is 60.

In certain embodiments, the invention relates to any of the compounds described herein, wherein n is 1, 2, or 3; preferably, n is 2.

In certain embodiments, the invention relates to any of the compounds described herein, wherein $A^1$ is an amine protecting group selected from an N,O-acetal, allyloxycarbonyl (Aloc), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain other embodiments, the invention relates to any of the compounds described herein, wherein $A^1$ is a protein, preferably an antibody.

In some embodiments, the invention relates to any of the compounds described herein, wherein $A^2$ is an —O-(carboxylate protecting group), and the carboxylate protecting group is selected from allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In some other embodiments, the invention relates to any of the compounds described herein, wherein $A^2$ is a protein, preferably an antibody.

In certain embodiments, the invention relates to any of the compounds described herein, wherein $A^1$ or $A^2$ is methionine, or $A^1$ or $A^2$ is a peptide comprising a methionine residue, an oligopeptide comprising a methionine residue, a polypeptide comprising a methionine residue, or a protein comprising a methionine residue.

In other embodiments, the invention relates to any of the compounds described herein, wherein $A^1$ or $A^2$ is cysteine, or $A^1$ or $A^2$ is a peptide comprising a cysteine residue, an oligopeptide comprising a cysteine residue, a polypeptide comprising a cysteine residue, or a protein comprising a cysteine residue.

In certain embodiments, the invention relates to any of the compounds described herein, wherein the compound of formula I is an antibody.

In some embodiments, the invention relates to any of the compounds described herein, for example, in a scheme, an equation, an example, or a figure.

Exemplary Peptides, Oligopeptides, Polypeptides, and Proteins

In certain embodiments, the invention relates to a peptide, an oligopeptide, a polypeptide, or a protein, wherein the peptide, oligopeptide, polypeptide, or protein comprises substructure I

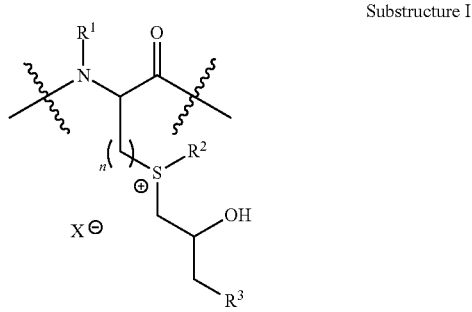

Substructure I wherein,
$R^1$ is H or alkyl;
$R^2$ is alkyl;
$R^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido;
n is 1-4, inclusive; and
X is a monovalent anion.

In certain embodiments, the invention relates to any of the peptides, oligopeptides, polypeptides, or proteins described herein, wherein the peptide, oligopeptide, polypeptide, or protein comprises a plurality of substructures I.

In certain embodiments, the invention relates any of the peptides, oligopeptides, polypeptides, or proteins described herein, wherein $R^1$ is preferably H.

In certain embodiments, the invention relates to any of the peptides, oligopeptides, polypeptides, or proteins described herein, wherein $R^1$ is alkyl, for example, methyl or ethyl.

In certain embodiments, the invention relates to any of the peptides, oligopeptides, polypeptides, or proteins described herein, wherein $R^2$ is methyl, ethyl, n-propyl, or n-butyl; preferably, $R^2$ is methyl.

In certain embodiments, the invention relates to any of the peptides, oligopeptides, polypeptides, or proteins described herein, wherein $R^3$ is substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido.

In certain embodiments, the invention relates to any of the peptides, oligopeptides, polypeptides, or proteins described herein, wherein $R^3$ is unsubstituted amino, unsubstituted alkyl, unsubstituted alkyloxy, azido, unsubstituted aryl, unsubstituted heteroaryl, halo, unsubstituted allyloxy, unsubstituted alkylcarbonyloxy, unsubstituted phosphonate, unsubstituted carbamate, or unsubstituted amido.

In certain embodiments, the invention relates to any of the compounds described herein, wherein $R^3$ is substituted amino, substituted alkyl, substituted alkyloxy, substituted aryl, substituted heteroaryl, substituted allyloxy, substituted alkylcarbonyloxy, substituted phosphonate, substituted carbamate, or substituted amido.

In certain embodiments, the invention relates to any of the peptides, oligopeptides, polypeptides, or proteins described herein, wherein $R^3$ is substituted alkyloxy, for example, heterocycloalkyloxy, phosphonate-substituted alkyloxy, acyloxyalkyloxy, aminoalkyloxy, aminoalkylamidoalkyloxy, or alkyloxycarbonylalkyloxy.

In certain embodiments, the invention relates to any of the peptides, oligopeptides, polypeptides, or proteins described herein, wherein $R^3$ is -L-halo, -L-azide, -L-$NHR^1$, -L-$NR^1$-TFA, -L-$NR^1$—C(O)—$CH_2$—$NR^1$-TFA, -L-O—$CH_2$—CH=$CH_2$, -L-O—$CH_2$CCH, -L-O-alkyl, -L-O—C(O)-alkyl, -L-P(O)(O-alkyl)$_2$, -L-P(O)(OH)$_2$, -L-O—C(O)—C(halo)(alkyl)$_2$, -L-$CH_2$—P(O)(O-alkyl)$_2$, -L-$CH_2$—P(O)(OH)$_2$, -L-O—$CH_2$CH—(C(O)$NR^1$-alkyl)($NR^1$-TFA), -L-O—$CH_2$CH—(C(O)$OR^1$)($NR^1$-TFA), -L-$OCH_2$—C(O)—$OR^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

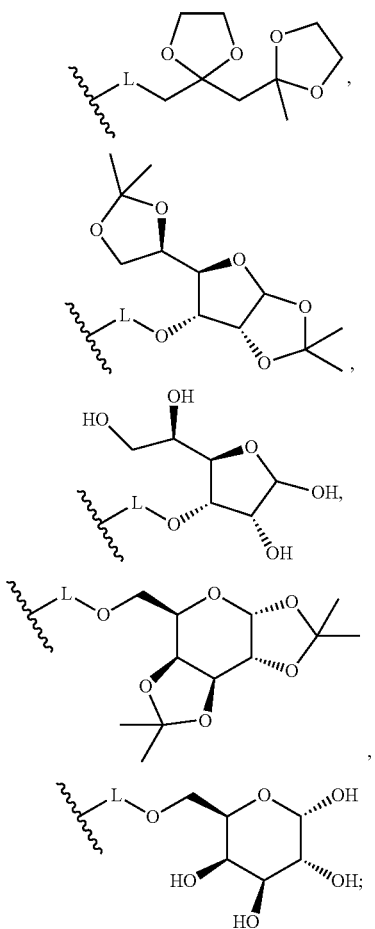

L is a bond or —(OCH$_2$CH$_2$)$_x$—, and x is 1-10.

In certain embodiments, the invention relates to any of the peptides, oligopeptides, polypeptides, or proteins described herein, wherein x is 1, 2, 3, 4, 5, or 6; preferably, x is 2, 3, or 4.

In certain embodiments, the invention relates to any of the peptides, oligopeptides, polypeptides, or proteins described herein, wherein m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, m is 1. In other embodiments, m is 60.

In certain embodiments, the invention relates to any of the peptides, oligopeptides, polypeptides, or proteins described herein, wherein n is 1, 2, or 3; preferably, n is 2.

In certain embodiments, the invention relates to any of the peptides, oligopeptides, polypeptides, or proteins described herein.

Exemplary Methods

In certain embodiments, the invention relates to a method for chemically modifying a peptide, oligopeptide, polypeptide, or protein by alkylation of one or more thioether groups comprising the steps of:

contacting a compound of formula II with an aqueous or polar organic solvent

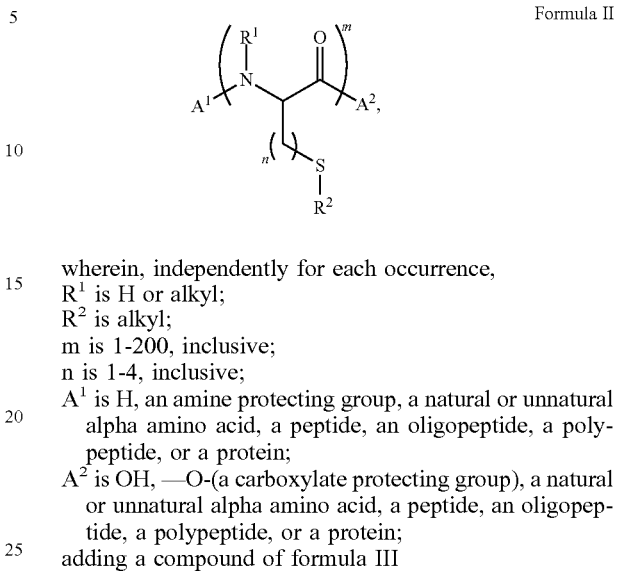

wherein, independently for each occurrence,
R$^1$ is H or alkyl;
R$^2$ is alkyl;
m is 1-200, inclusive;
n is 1-4, inclusive;
A$^1$ is H, an amine protecting group, a natural or unnatural alpha amino acid, a peptide, an oligopeptide, a polypeptide, or a protein;
A$^2$ is OH, —O-(a carboxylate protecting group), a natural or unnatural alpha amino acid, a peptide, an oligopeptide, a polypeptide, or a protein;
adding a compound of formula III Formula III wherein, independently for each occurrence,
R$^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido; and
reacting the compound of formula II with the compound of formula III, thereby creating a compound of formula I Formula I In certain embodiments, the invention relates to any of the methods described herein, wherein the compound of formula II is suspended in an aqueous or polar organic solvent. In other embodiments, the compound of formula II is dissolved in an aqueous or polar organic solvent. In even other embodiments, the compound of formula II is mixed with an aqueous or polar organic solvent.

In certain embodiments, the invention relates to any of the methods described herein, wherein R¹ is preferably H.

In certain embodiments, the invention relates to any of the methods described herein, wherein R¹ is alkyl, for example, methyl or ethyl.

In certain embodiments, the invention relates to any of the methods described herein, wherein R² is methyl, ethyl, n-propyl, or n-butyl; preferably, R² is methyl.

In certain embodiments, the invention relates to any of the methods described herein, wherein R³ is substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido.

In certain embodiments, the invention relates to any of the methods described herein, wherein R³ is unsubstituted amino, unsubstituted alkyl, unsubstituted alkyloxy, azido, unsubstituted aryl, unsubstituted heteroaryl, halo, unsubstituted allyloxy, unsubstituted alkylcarbonyloxy, unsubstituted phosphonate, unsubstituted carbamate, or unsubstituted amido.

In certain embodiments, the invention relates to any of the methods described herein, wherein R³ is substituted amino, substituted alkyl, substituted alkyloxy, substituted aryl, substituted heteroaryl, substituted allyloxy, substituted alkylcarbonyloxy, substituted phosphonate, substituted carbamate, or substituted amido.

In certain embodiments, the invention relates to any of the methods described herein, wherein R³ is substituted alkyloxy, for example, heterocycloalkyloxy, phosphonate-substituted alkyloxy, acyloxyalkyloxy, aminoalkyloxy, aminoalkylamidoalkyloxy, or alkyloxycarbonylalkyloxy.

In certain embodiments, the invention relates to any of the methods described herein, wherein R³ is -L-halo, -L-azide, -L-NHR¹, -L-NR¹-TFA, -L-NR¹—C(O)—CH₂—NR¹-TFA, -L-O—CH₂—CH═CH₂, -L-O—CH₂CCH, -L-O-alkyl, -L-O—C(O)-alkyl, -L-P(O)(O-alkyl)₂, -L-P(O)(OH)₂, -L-O—C(O)—C(halo)(alkyl)₂, -L-CH₂—P(O)(O-alkyl)₂, -L-CH₂—P(O)(OH)₂, -L-O—CH₂CH—(C(O)NR¹-alkyl)(NR¹-TFA), -L-O—CH₂CH—(C(O)OR¹)(NR¹-TFA), -L-OCH₂—C(O)—OR¹, -L-CH—(CO₂-alkyl)₂, -L-CH—(CO₂H)₂, -L-SO₂(O-alkyl), -L-SO₂(O-aryl), -L-SO₃H,

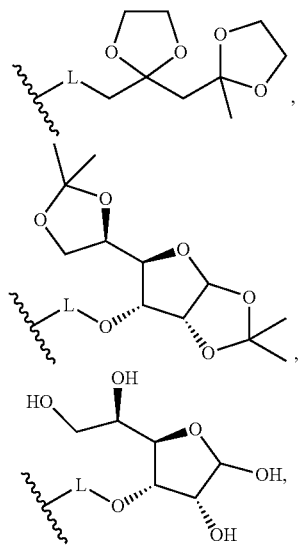

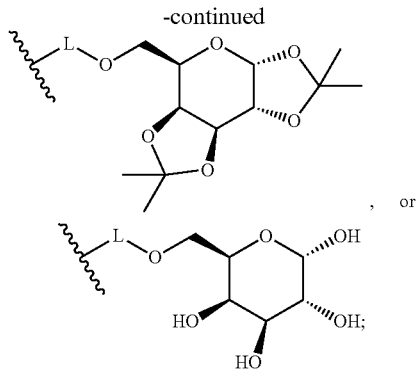

L is a bond or —(OCH₂CH₂)ₓ—, and x is 1-10.

In certain embodiments, the invention relates to any of the methods described herein, wherein x is 1, 2, 3, 4, 5, or 6; preferably, x is 2, 3, or 4.

In certain embodiments, the invention relates to any of the methods described herein, wherein m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In some embodiments, m is 1. In other embodiments, m is 60.

In certain embodiments, the invention relates to any of the methods described herein, wherein n is 1, 2, or 3; preferably, n is 2.

In certain embodiments, the invention relates to any of the methods described herein, wherein A¹ is an amine protecting group selected from an N,O-acetal, allyloxycarbonyl (Aloc), benzyl (Bn), benzyloxycarbonyl (Cbz), benzyloxymethyl (BOM), t-butoxycarbonyl (Boc), t-butyldimethylsilyl (TBDMS), t-butyldiphenylsilyl (TBDPS), diphenylmethyl, diphenylmethylene, ethoxycarbonyl, 9-fluorenylmethoxycarbonyl (Fmoc), p-methoxybenzyl (PMB), methoxycarbonyl, methoxymethyl (MOM), p-methoxyphenyl (PMP), p-nitrocinnamyloxycarbonyl (Noc), tosyl (Ts), 2-tosylethoxycarbonyl (Tsoc), 2,2,2-trichloroethoxycarbonyl (Troc), trifluoroacetyl, triisopropylsilyl (TIPS), trimethylsilyl (TMS), 2-(trimethylsilyl)ethoxycarbonyl (Teoc), 2-(trimethylsilyl)ethoxymethyl (SEM), or trityl (Tr).

In certain other embodiments, the invention relates to any of the methods described herein, wherein A¹ is a protein, preferably an antibody.

In some embodiments, the invention relates to any of the methods described herein, wherein A² is an —O-(carboxylate protecting group), and the carboxylate protecting group is selected from allyl, benzyl, benzyloxymethyl (BOM), t-Bu, t-butyldimethylsilyl (TBDMS), t-butyldiphenylsilyl (TBDPS), diphenylmethyl, 9-fluorenylmethyl (Fm), 2-methoxyethoxymethyl (MEM), methoxymethyl (MOM), p-nitrobenzyl (PNB), an ester, a 1,3-oxazoline, pivaloyloxymethyl (Pom), 2-tosylethyl (TSE), 2,2,2-trichloroethyl (TCE), triethylsilyl (TES), trimethylsilyl (TMS), 2-(trimethylsilyl)ethoxymethyl (SEM), or 2-(trimethylsilyl)ethyl (TMSE).

In other embodiments, the invention relates to any of the methods described herein, wherein A² is a protein, preferably an antibody.

In certain embodiments, the invention relates to any of the methods described herein, wherein A¹ or A² is methionine, or A¹ or A² is a peptide comprising a methionine residue, an oligopeptide comprising a methionine residue, a polypeptide comprising a methionine residue, or a protein comprising a methionine residue.

In other embodiments, the invention relates to any of the methods described herein, wherein $A^1$ or $A^2$ is cysteine, or $A^1$ or $A^2$ is a peptide comprising a cysteine residue, an oligopeptide comprising a cysteine residue, a polypeptide comprising a cysteine residue, or a protein comprising a cysteine residue.

In certain embodiments, the invention relates to any of the methods described herein, wherein the compound of formula II is an antibody.

In certain embodiments, the invention relates to any of the methods described herein, wherein the compound of formula I is an antibody.

In certain embodiments, the invention relates to any of the methods described herein, wherein the pH of the aqueous or polar organic solvent is less than about 3. In other embodiments, the invention relates to any of the methods described herein, wherein the pH of the aqueous or polar organic solvent is about 2.5, about 2.0, about 1.5, about 1.0, or about 0.5.

In certain embodiments, the invention relates to any of the methods described herein, wherein the mole ratio of the compound of formula III to the compound of formula II is from about 5:1 to about 1.5:1, for example, about 5:1, about 4.5:1, about 4:1, about 3.5:1, about 3:1, about 2.5:1, about 2:1, or about 1.5:1, preferably about 3:1, about 2.5:1, about 2:1, or about 1.5:1.

In certain embodiments, the invention relates to any of the methods described herein, wherein the temperature of the aqueous or polar organic solvent is from about 20° C. to about 40° C., for example about 30° C., about 31° C., about 32° C., about 33° C., about 34° C., about 35° C., about 36° C., about 37° C., about 38° C., about 39° C., or about 40° C., preferably about 37° C.

In certain embodiments, the invention relates to any of the methods described herein, wherein the aqueous or polar organic solvent is preferably glacial AcOH.

For example, the inventive methods may be used to modify at least one amino acid residue of a peptide, an oligopeptide, a polypeptide, or a protein, regardless of whether the amino acid residue to be modified is found at the N-terminus, the C-terminus, or in the middle of the sequence of amino acids of the peptide, oligopeptide, polypeptide, or protein.

In various embodiments, the invention relates to a compound formed by any of the methods or processes described herein.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "heteroatom" is art-recognized and refers to an atom of any element other than carbon or hydrogen. Illustrative heteroatoms include boron, nitrogen, oxygen, phosphorus, sulfur and selenium.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "amido" as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "amino" as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carbonyl" as used herein, means a —C(=O)— group.

The term "carboxy" as used herein, means a —CO$_2$H group.

The term "cyano" as used herein, means a —CN group.

The term "halo" or "halogen" means —Cl, —Br, —I or —F.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkyl sulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkyl sulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "silyl" as used herein includes hydrocarbyl derivatives of the silyl (H$_3$Si—) group (i.e., (hydrocarbyl)$_3$SH, wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethyl silyl)ethoxy]methyl (SEM).

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The following examples include experimental procedures and spectral data for sample compounds, procedures for alkylation reactions, and methods for stability studies.

General Materials and Methods

Unless otherwise stated, all polymer functionalization reactions were performed in glass vials, under ambient atmosphere. Small molecule reactions were performed under $N_2$ using oven dried glassware. Reactions at elevated temperature were controlled using a Corning PC 420D thermostated hotplate equipped with a thermocouple probe. Room temperature reactions were performed at ca. 20° C. ambient temperature. THF and $CH_2Cl_2$ were degassed by sparging with $N_2$ and dried by passing through alumina columns. Commercial anhydrous DMF was used as received. Fisher ACS grade glacial AcOH was used as received. The PHCKRM peptide was obtained from NeoBioLab and was reported 96.7% pure. Poly(S-methylmethionine sulfonium chloride), $M^{Me}$, and poly(S-benzylmethionine sulfonium chloride), $M^{Bn}$, were prepared as previously described.[15] Allyl alcohol was dried by storing over 3 Å molecular sieves. All other reagents were used as received. Dialysis was performed using deionized water (18.2 MΩ-cm) prepared by passing in-house deionized water through a Millipore Milli-Q Biocel A10 unit. In all other cases, in-house reverse osmosis purified water was used. Thin-layer chromatography was performed with EMD gel 60 F254 plates (0.25 mm thickness) and visualized using a UV lamp or permanganate stain. Column chromatography was performed using Silicycle Siliaflash G60 silica (60-200 μm). Chromatography eluents are reported as volume percent. Dialysis was performed using regenerated cellulose dialysis tubing obtained from Spectrum Labs. NMR spectra were recorded on either a Bruker AV400 or AV300 instrument with chemical shifts reported relative to solvent signal. Abbreviations of splitting pattern designations are listed in the abbreviation section. ESI-MS was performed using a Waters LCT Premier spectrometer. Small molecule samples were prepared in MeOH (1 mg/mL) and injected at a rate of 20 μL/min. Peptide samples (5 mM) were analyzed analogously using a 50% $MeCN/H_2O$ matrix.

Abbreviations: N-carboxyanhydride (NCA), degree of polymerization (DP), L-methionine (Met), poly(L-methionine) (M), N,N,N',N',N"-pentamethyldiethylenetriamine (PMDTA), potassium tert-butoxide (KOtBu), glacial acetic acid (AcOH), 2,6-bis(1,1-dimethylethyl)-4-methylphenol (BHT), ethanol (EtOH), ethyl acetate (EtOAc), diethyl ether ($Et_2O$), tetrahydrofuran (THF), trifluoroacetic acid (TFA), meta-chloroperbenzoic acid (mCPBA), hexafluoroisopropanol (HFIP), ethylene oxide (EO), molecular weight cut-off (MWCO), room temperature (RT), equivalents (eq), methanol (MeOH), liquid dinitrogen ($LN_2$), N,N-dimethylformamide (DMF), broad (br), doublet (d), doublet of doublets (dd), doublet of doublet of doublets (ddd), doublet of multiplets (dm), doublet of quartets (dq), doublet of triplets (dt), quartet (q), septet (sep), singlet (s), triplet (t), thin layer chromatography (TLC), electrospray ionization-mass spectrometry (ESI-MS)

General Synthetic Procedures

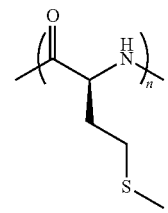

Poly(L-methionine)$_{60}$, $M_{60}$

Prepared by previously reported method. Kramer, J. R.; Deming, T. J. *Biomacromolecules* 2012, 13, 1719-1723. Met NCA was polymerized with $Co(PMe_3)_4$ using a 20:1, monomer to initiator ratio. The DP was determined by endcapping a small aliquot from the polymerization mixture with 2 kDa PEG-isocyanate ($CH_3(OCH_2CH_2)_{45}N\!=\!C\!=\!O$) followed by $^1H$ NMR analysis. Found Composition, DP=59.

$M_{60}$ Alkylation Procedure A (Procedure A)

$M_{60}$ was suspended in glacial AcOH (16 mg/mL). The epoxide (3 eq per Met residue) was added in one portion. The mixture was stirred vigorously at 37° C. After 24 h, the limpid solution was transferred to a 2 kDa MWCO dialysis bag and dialyzed against 3 mM $HCl_{(aq)}$ (24 h, 3 $H_2O$ changes). The retentate was lyophilized, to provide the functionalized polypeptide.

$M_{60}$ Alkylation Procedure B (Procedure B)

$M_{60}$ was suspended in glacial AcOH (27 mg/mL). The epoxide (1.5 eq per Met residue) was added. The mixture was stirred vigorously at 37° C. After the peptide dissolved (ca. 2-6 h), a second portion of epoxide (1.5 eq per Met residue) was added. After 24 h, the limpid solution was transferred to a 2 kDa MWCO dialysis bag and dialyzed against 3 mM HCl$_{(aq)}$ (24 h, 3 H$_2$O changes). The retentate was lyophilized, to provide the functionalized polypeptide.

M$_{60}$ Glycosylation (Procedure C)

The procedure was analogous to Procedure B, however before transfer to the dialysis bag, 1 mL of 2 M HCl$_{(aq)}$ was added. The solution was allowed to stand at RT for 16 h. After dialysis and lyophilization, the deprotected, fully glycosylated peptide was recovered.

Alternative M$_{60}$ Alkylation Using 1.5 Eq of Epoxide 4a

M$_{60}$ (6.0 mg) was suspended in glacial AcOH (0.20 mL). 4a (3.4 mg, 0.034 mmol, 0.75 eq per Met residue) was added. The suspension was stirred vigorously at RT and became homogenous over 24 h. Another addition of 4a (3.4 mg, 0.034 mmol, 0.75 eq per Met residue) was performed and stirring was continued for an additional 24 h. The reaction mixture was transferred to a 2 kDa MWCO dialysis bag and dialyzed against 3 mM HCl$_{(aq)}$ (24 h, 3 H$_2$O changes). The retentate was lyophilized, to provide 4 (12 mg, 94% yield, >99% functionalized ($^1$H NMR)).

Alternative M$_{60}$ Alkylation in Aqueous Buffer Using Epoxide 4a

M$_{60}$ (8.0 mg), was suspended in H$_2$O (0.50 mL) with vigorous stirring at RT. NaH$_2$PO$_4$.H$_2$O (17 mg, 0.12 mmol) and Na$_2$HPO$_4$.7H$_2$O (16 mg, 0.061 mmol) were added, followed by 4a (18 mg, 0.18 mmol, 3 eq per Met residue). The mixture became completely limpid at 2 d and was stirred 3 d in total. The reaction mixture was transferred to a 2 kDa MWCO dialysis bag and dialyzed against 3 mM HCl$_{(aq)}$ (24 h, 3 H$_2$O changes). The retentate was lyophilized, to provide a partially functionalized material (14 mg, 77% functionalized ($^1$H NMR)).

Poly(S-Alkyl-L-Methionine) Stability Studies

Polymer stock solutions (25 mmol Met residue per mL) were prepared in H$_2$O. Buffers were prepared by titrating 0.1 M solutions of the parent acid with 1 N NaOH. PBS 10× was prepared by dissolving a PBS tablet and adjusted to pH 7.4. The polymer stock (0.9 mL) was diluted with the buffer stock (0.1 mL) and if necessary, nucleophile (0.1 mmol) was added. The mixture was incubated on a 37° C. H$_2$O bath for 24 h. The solution was transferred to a 2 kDa MWCO dialysis bag and dialyzed against 3 mM HCl$_{(aq)}$ (24 h, 3 H$_2$O changes). The retentate was lyophilized. The products were analyzed by $^1$H NMR, and the ratio of S-alkyl-Met/Met was determined. In all studies of 4, 8 and poly(S-methylmethionine sulfonium chloride), mass recoveries were greater than 90%.

Example 1

Synthesis of Sulfonium Polymers

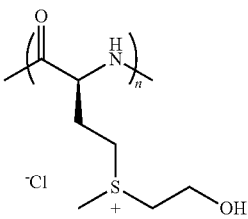

Poly(S-(2-hydroxyethyl)-L-methionine sulfonium chloride), 1

Prepared from M$_{60}$ and 1a using Procedure A. The reaction was conducted in a sealed glass ampule. $^1$H NMR (300 MHz, D$_2$O, 25° C.): δ 4.70-4.53 (br m, 1H), 4.22-4.00 (br m, 2H), 3.81-3.41 (br m, 4H), 3.05 (d, J=3.1 Hz, 3H), 2.58-2.20 (br m, 2H).

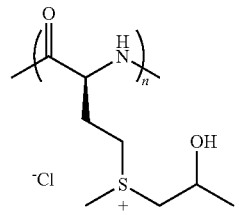

Poly(S-(2-hydroxypropyl)-L-methionine sulfonium chloride), 2

Prepared from M$_{60}$ and 2a using Procedure A. The product contained 6% ($^1$H NMR) of the 1-hydroxypropan-2-yl regioisomer. $^1$H NMR (400 MHz, D$_2$O, 25° C.): δ 4.72-4.53 (br m, 1H), 4.48-4.29 (br m, 1H), 3.81-3.39 (br m, 4H), 3.24-2.91 (br m, 3H), 2.62-2.23 (br m, 2H), 1.68-1.33 (m, 3H).

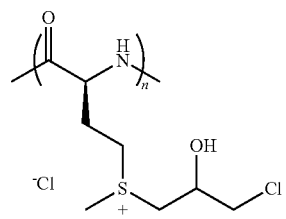

Poly(S-(3-chloro-2-hydroxypropyl)-L-methionine sulfonium chloride), 3

Prepared from M$_{60}$ and 3a using Procedure A. $^1$H NMR (400 MHz, D$_2$O, 25° C.): δ 4.71-4.59 (br m, 1H), 4.59-4.44 (br m, 1H), 3.94-3.42 (br m, 6H), 3.20-3.00 (br m, 3H), 2.59-2.26 (br m, 2H).

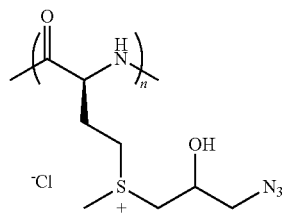

Poly(S-(3-azido-2-hydroxypropyl)-L-methionine sulfonium chloride), 4

Prepared from M$_{60}$ and 4a using Procedure A. $^1$H NMR (400 MHz, D$_2$O, 25° C.): δ 4.71-4.60 (br m, 1H), 4.51-4.37 (br m, 1H), 3.82-3.41 (br m, 6H), 3.21-3.00 (br m, 3H), 2.58-2.24 (br m, 2H).

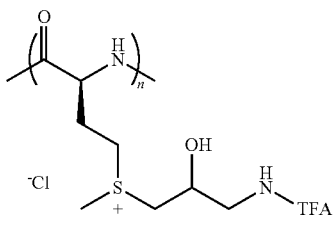

Poly(S-(2-hydroxy-3-(2,2,2-trifluoroacetamido)propyl)-L-methionine sulfonium chloride), 5

Prepared from $M_{60}$ and 5a using Procedure A. $^1$H NMR (400 MHz, D$_2$O, 25° C.): δ 4.71-4.48 (br m, 1H), 4.48-4.27 (br m, 1H) 3.96-3.33 (br m, 6H), 3.30-2.90 (br m, 3H) 2.81-2.72 (br m, 1H), 2.59-2.27 (br m, 2H). $^{19}$F NMR (376 MHz, D$_2$O, 25° C.): δ −72.92.

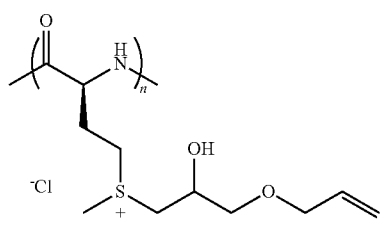

Poly(S-(3-(allyloxy)-2-hydroxypropyl)-L-methionine sulfonium chloride), 6

Prepared from $M_{60}$ and 6a using Procedure A. $^1$H NMR (400 MHz, D$_2$O, 25° C.): δ 6.07-5.90 (br m, 1H), 5.44-5.34 (br m, 1H), 5.34-5.26 (br m, 1H), 4.67-4.58 (br m, 1H), 4.47-4.32 (br m, 1H), 4.23-4.08 (br m, 2H), 3.81-3.40 (br m, 6H), 3.16-2.99 (br m, 3H), 2.56-2.23 (br m, 2H).

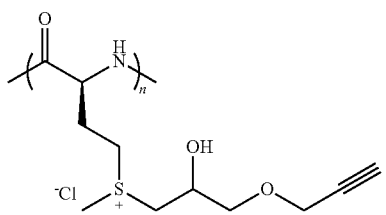

Poly(S-(2-hydroxy-3-(prop-2-yn-1-yloxy)propyl)-L-methionine sulfonium chloride), 7

Prepared from $M_{60}$ and 7a using Procedure A. $^1$H NMR (400 MHz, D$_2$O, 25° C.): δ 4.70-4.56 (br m, 1H), 4.52-4.38 (br m, 1H), 4.33 (s, 2H), 3.89-3.41 (br m, 6H), 3.23-3.04 (br m, 3H), 3.01 (s, 1H), 2.56-2.24 (br m, 2H).

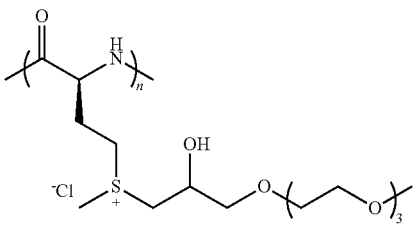

Poly(S-(2-hydroxy-4,7,10,13-tetraoxatetradecyl)-L-methionine sulfonium chloride), 8

Prepared from $M_{60}$ and 8a using Procedure A, alkylation was allowed to proceed 36 h. $^1$H NMR (400 MHz, D$_2$O, 25° C.): δ 4.74-4.56 (br m, 1H), 4.53-4.32 (br m, 1H), 3.97-3.36 (br m, 21H), 3.31-2.97 (br m, 3H), 2.66-2.16 (br m, 2H).

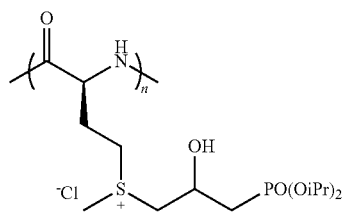

Poly(S-(3-(diisopropoxyphosphoryl)-2-hydroxypropyl)-L-methionine sulfonium chloride), 9

Prepared from $M_{60}$ and 9a using Procedure A. The product was found to be 74% functionalized ($^1$H NMR). $^1$H NMR (300 MHz, D$_2$O, 25° C.): δ 4.68-4.42 (br m, 2H), 3.87-3.38 (br m, 4H), 3.19-3.00 (br m, 3H), 2.72-2.54 (br m, 1.1H), 2.53-2.21 (br m, 4H), 2.20-2.00 (br m, 2.6H), 1.53-1.25 (d, J=4.2 Hz, 12H). Note: Peaks arising from unfunctionalized Met residues are italicized.

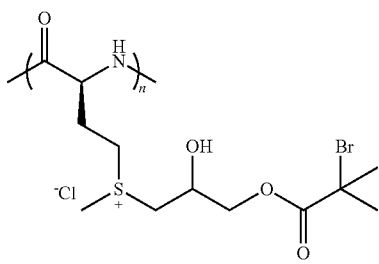

Poly(S-(3-((2-bromo-2-methylpropanoyl)oxy)-2-hydroxypropyl)-L-methionine sulfonium chloride), 10

Prepared from $M_{60}$ and 10a using Procedure A. The product was found to be 52% functionalized ($^1$H NMR). $^1$H NMR (400 MHz, D$_2$O, 25° C.): δ 4.68-4.50 (br m, 1H), 4.50-4.31 (br m, 1H), 3.87-3.40 (br m, 4H), 3.30-3.03 (br m, 3H), 2.82-2.56 (br m, 2.4H), 2.57-2.27 (br m, 2H), 2.27-2.07 (br m, 4.9H), 2.07-1.89 (s, 6H). Note: Peaks arising from unfunctionalized Met residues are italicized.

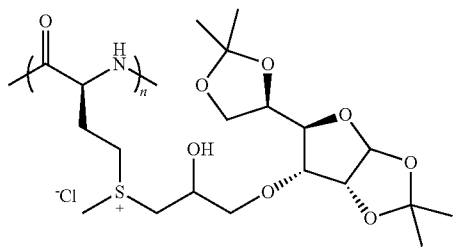

Poly(S-((3-(1,2:5,6-Di-O-isopropylidene-3-deoxy-α-D-glucofuranosid-3-yl)oxy)-2-hydroxypropyl)-L-methionine sulfonium chloride), 11

Prepared from M$_{60}$ and 12a using Procedure A. The product was found to be 54% functionalized ($^1$H NMR). $^1$H NMR (400 MHz, D$_2$O, 25° C.): δ 6.17-5.97 (br m, 1H), 5.02-4.87 (br m, 1H), 4.67-3.41 (br m, 13H), 3.23-2.94 (br m, 3H), 2.81-2.55 (br m, 1.8H), 2.56-2.26 (br m, 2H), 2.26-1.93 (br m, 4.3H), 1.74-1.28 (br m, 12H). Note: Peaks arising from unfunctionalized Met residues are italicized.

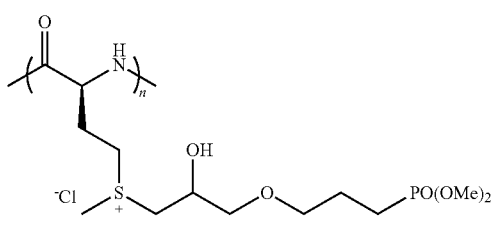

Poly(S-(3-(3-(dimethoxyphosphoryl)propoxy)-2-hydroxypropyl)-L-methionine sulfonium chloride), 12

Prepared from M$_{60}$ and 12a using Procedure B. $^1$H NMR (400 MHz, D$_2$O, 25° C.): δ 4.72-4.53 (br m, 1H), 4.48-4.31 (br m, 1H), 3.96-3.75 (d, J=10.9 Hz, 6H) 3.75-3.36 (br m, 8H), 3.21-2.96 (br m, 3H), 2.59-2.21 (br m, 2H), 2.10-1.96 (br m, 2H), 1.96-1.80 (br m, 2H).

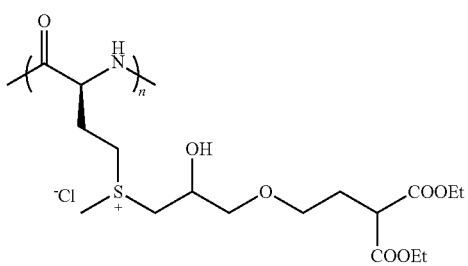

Poly(S-(3-(2-(1,3-diethoxy-1,3-dioxopropan-2-yl)ethoxy)-2-hydroxypropyl)-L-methionine sulfonium chloride), 13

Prepared from M$_{60}$ and 13a using Procedure B. $^1$H NMR (400 MHz, D$_2$O, 25° C.): δ 4.69-4.53 (br m, 1H), 4.45-4.32 (br m, 1H), 4.32-4.18 (br m, 4H), 3.84-3.38 (br m, 9H), 3.21-2.98 (br m, 3H), 2.58-2.27 (br m, 2H), 2.27-2.14 (br m, 2H), 1.42-1.18 (t, J=7.1 Hz, 6H).

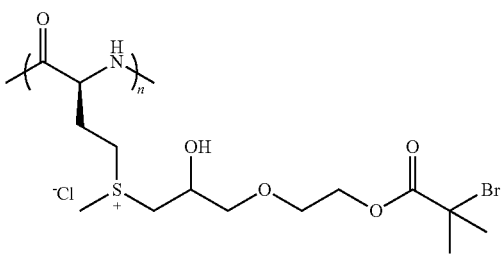

Poly(S-(2-hydroxy-3-((2-(2-bromo-2-methylpropanoyl)oxy)ethanoxy)propyl)-L-methionine sulfonium chloride), 14

Prepared from M$_{60}$ and 14a using Procedure B. $^1$H NMR (400 MHz, D$_2$O, 25° C.): δ 4.71-4.59 (br m, 1H), 4.50-4.35 (br m, 3H), 3.98-3.83 (br m, 2H), 3.82-3.41 (br m, 6H), 3.19-3.01 (br m, 3H), 2.58-2.25 (br m, 2H), 2.10-1.89 (br m, 6H).

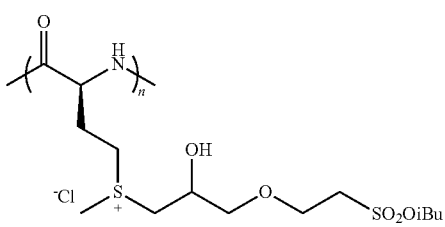

Poly(S-(2-hydroxy-3-(2-(isobutoxysulfonyl)ethanoxy)propyl)-L-methionine sulfonium chloride), 15

Prepared from M$_{60}$ and 15a using Procedure B. Recovered product was found to be 11% deprotected ($^1$H NMR). $^1$H NMR (400 MHz, D$_2$O, 25° C.): δ 4.72-4.58 (br m, 1H), 4.46-4.34 (br m, 1H), 4.19 (d, J=6.3 Hz, 2H), 4.07 (m, 2H), 3.82-3.41 (br m, 8H), 3.15-2.98 (br m, 3H), 2.51-2.25 (br m, 2H), 2.08 (sep, J=7.2 Hz, 1H), 1.01 (d, J=7.0 Hz, 6H).

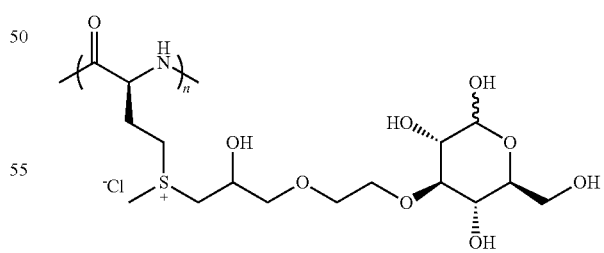

Poly(S-((3-(2-(3-deoxy-D-glucopyranosid-3-yl)oxy)ethoxy)-2-hydroxypropyl)-L-methionine sulfonium chloride), 16

Prepared from M$_{60}$ and 16a using Procedure C. The product was found to contain a 3:7 ratio of α:β anomers ($^1$H NMR) in D$_2$O at 25° C. $^1$H NMR (400 MHz, D$_2$O, 25° C.):

δ 5.30-5.19 (br m, 0.3H), 4.72-4.52 (br m, 1.7H), 4.50-4.32 (br m, 1H), 4.12-3.96 (br m, 2H), 3.96-3.26 (br m, 14H), 3.23-2.94 (br m, 3H), 2.59-2.22 (br m, 1H).

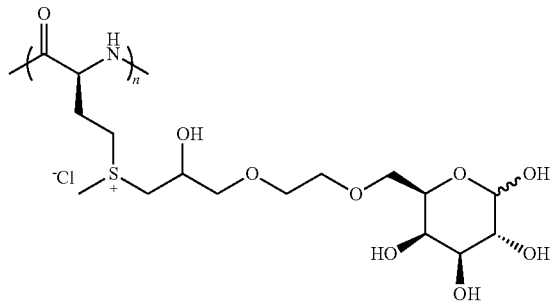

Poly(S-((3-(2-(6-deoxy-D-galactopyranosid-6-yl)oxy)ethoxy)-2-hydroxypropyl)-L-methionine sulfonium chloride), 17

Prepared from $M_{60}$ and 17a using Procedure C. The product was found to contain a 3:7 ratio of α:β anomers ($^1$H NMR) in $D_2O$ at RT. $^1$H NMR (400 MHz, $D_2O$, 25° C.): δ 5.31-5.26 (d, J=5.6 Hz, 0.3H), 4.70-4.56 (br m, 1.7H), 4.49-4.32 (br m, 1H), 4.10-3.39 (br m, 16H), 3.20-2.97 (br m, 3H), 2.56-2.23 (br m, 2H).

Example 2

Deprotection of Functional Sulfonium Polypeptides

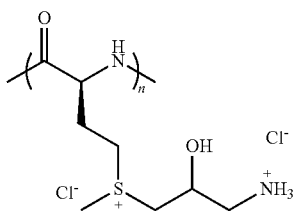

Poly(S-(3-ammonio-2-hydroxypropyl)-L-methionine sulfonium dichloride)

A solution of 5 (18 mg, 0.048 mmol) in $H_2O$ (1.5 mL) was treated with $K_2CO_3$ (10 mg, 0.072 mmol). The solution was allowed to stand 24 h. The solution was transferred to a 2 kDa MWCO dialysis bag and dialyzed against 3 mM $HCl_{(aq)}$ (24 h, 3 $H_2O$ changes). The retentate was lyophilized, to provide the deprotected polypeptide (14 mg, 93% yield) which was found to be fully deprotected ($^{19}$F NMR).

Alternate Method: A solution of 5 (8.0 mg, 0.023 mmol) in absolute EtOH (0.5 mL) was stirred at RT. $NaBH_4$ (5.0 mg, 0.125 mmol) was added and the solution was stirred vigorously for 30 min. Another portion of $NaBH_4$ (5.0 mg, 0.125 mmol) was added and the suspension was allowed to stir an additional 30 min. The suspension was acidified with dilute $HCl_{(aq)}$ and transferred to a 2 kDa MWCO dialysis bag and dialyzed against 3 mM $HCl_{(aq)}$ (24 h, 3 $H_2O$ changes). The retentate was lyophilized, to provide the deprotected polypeptide (6.9 mg, 95% yield) which was found to be fully deprotected ($^{19}$F NMR).

$^1$H NMR (400 MHz, $D_2O$, 25° C.): δ 4.712-4.45 (br m, 2H), 3.90-3.46 (br m, 4H), 3.41-3.04 (br m, 5H), 2.60-2.25 (br m, 2H). $^{19}$F NMR (376 MHz, $D_2O$, 25° C.): No Peaks.

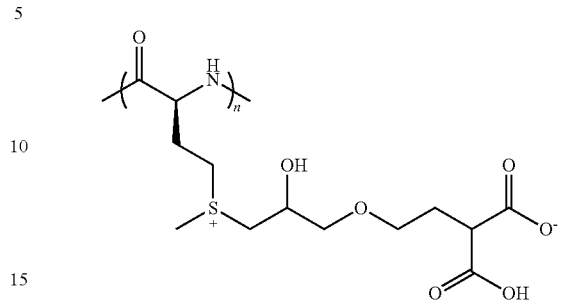

Poly(S-(3-(2-(1-Hydroxy-3-oxido-1,3-dioxopropan-2-yl)ethoxy)-2-hydroxypropyl)-L-methionine sulfonium)

A solution of 13 (8.9 mg, 0.021 mmol) in $H_2O$ (0.4 mL), was treated with 1 N $NaOH_{(aq)}$ (0.15 mL, 0.15 mmol). The solution was allowed to stand 16 h at 4° C. The solution was acidified with dilute $HCl_{(aq)}$, transferred to a 2 kDa MWCO dialysis bag and dialyzed against 3 mM $HCl_{(aq)}$ (24 h, 3 $H_2O$ changes). The retentate was lyophilized to provide the deprotected polypeptide (6.7 mg, 96% yield) which was found to be >99% deprotected ($^1$H NMR).

Alternate Method: The deprotection was conducted as above, with 1 N $NaOH_{(aq)}$ (0.10 mL, 0.10 mmol) at RT for 4 h. The polypeptide (6.7 mg, 96% yield) was found to be >97% deprotected ($^1$H NMR).

$^1$H NMR (400 MHz, $D_2O$, 25° C.): 4.69-4.50 (br m, 1H), 4.50.4.43 (br m, 1H), 3.82-3.34 (br m 8H), 3.06 (m, 3H), 2.60-2.06 (br m, 4H).

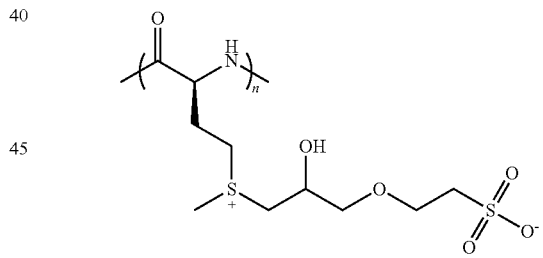

Poly(S-(2-hydroxy-3-(2-(oxidosulfonyl)ethanoxy)propyl)-L-methionine sulfonium chloride)

A solution of 15 (8.0 mg, 0.020 mmol) was dissolved in 10% (w/v) $NaN_3$ $_{(aq)}$ (0.5 mL). The solution was stirred for 24 h on a 37° C. $H_2O$ bath. The solution was transferred to a 2 kDa MWCO dialysis bag and dialyzed against 3 mM $HCl_{(aq)}$ (24 h, 3 $H_2O$ changes). The retentate was lyophilized, to provide the deprotected polypeptide (5.7 mg, 91% yield) which was found to be >99% deprotected ($^1$H NMR). $^1$H NMR (400 MHz, $D_2O$, 25° C.): δ 4.67-4.55 (br m, 1H), 4.47-4.34 (br m, 1H), 4.03 (m, 2H), 3.81-3.38 (br m, 6H), 3.24 (t, J=5.7 Hz, 2H), 3.04 (m, 3H), 2.54-2.23 (br m, 2H).

Note: Deprotection under the same conditions with 10% NaI provided a 77% deprotected material. Using 0.67 M HBr: 60% deprotection. In all cases no side products due to sulfonium decomposition were observed.

Example 3

Further Functionalization of Functional Sulfonium Polypeptides

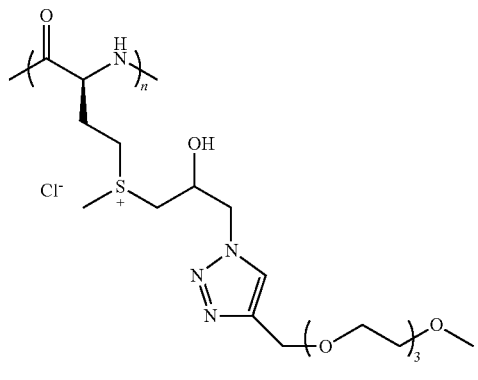

Poly(S-(2-hydroxy-3-(4-(2,5,8,11-tetraoxadodecyl)-1H-1,2,3-triazol-1-yl)propyl)-L-methionine sulfonium chloride A solution of 4 (15 mg, 0.056 mmol azide), 2,5,8,11-tetraoxatetradec-13-yne (21 mg, 0.10 mmol) and sodium ascorbate (5.0 mg, 0.025 mmol) was degassed in $H_2O$ (0.50 mL) by stirring under $N_2$ for 1 hr. A separate solution of PMDTA (2.0 μL, 0.010 mmol) and $CuSO_4 \cdot 5H_2O$ (1.3 mg, 0.0051 mmol) in $H_2O$ (0.50 mL) was degassed analogously. The copper solution was added to the azide solution and stirring of the mixture was continued for 24 h. The solution was transferred to a 2 kDa MWCO dialysis bag and dialyzed against 3 mM $HCl_{(aq)}$ (36 h, 5 $H_2O$ changes). The retentate was filtered through a 0.45 μM syringe filter and lyophilized, to provide the completely PEGylated polypeptide (19 mg, 89% yield). $^1$H NMR (400 MHz, $D_2O$, 25° C.): δ 8.27-7.95 (br s, 1 H), 4.75-4.56 (br m, 4H), 3.83-3.54 (br m, 18H), 3.38 (s, 3H), 3.13-3.00 (br m, 3H), 2.55-2.23 (br m, 2H).

Example 4

Chemoselectivity of Met Alkylations

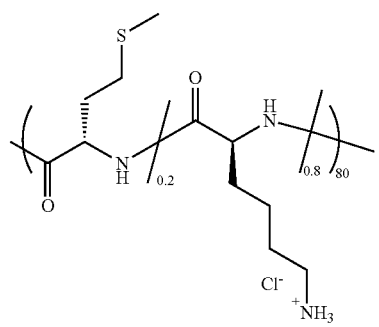

Poly[(L-methionine)$_{0.2}$-stat-(L-lysine hydrochloride)$_{0.8}]_{80}$, $(M_{0.2}K_{0.8})_{80}$ Prepared by previously reported method. Kramer, J. R.; Deming, T. J. Biomacromolecules 2012, 13, 1719-1723. Briefly, ε-TFA-lysine NCA and Met NCA were polymerized with $Co(PMe_3)_4$ using a 30:1, monomer to initiator ratio. The polymer was deprotected using $K_2CO_3$/MeOH followed by dialysis and cation exchange. DP was determined by endcapping a small aliquot from the polymerization mixture with 2 kDa PEG-isocyanate $(CH_3(OCH_2CH_2)_{45}N=C=O)$ followed by $^1$H NMR analysis. Found composition: $(M_{0.2}K_{0.8})_{82}$.

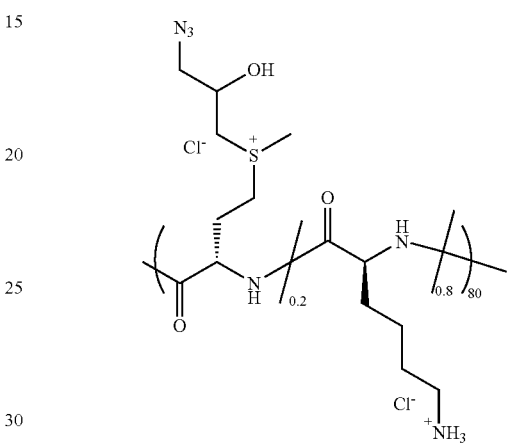

Poly[(S-(3-azido-2-hydroxypropyl)-L-methionine sulfonium chloride)$_{0.2}$-stat-(L-lysine hydrochloride)$_{0.8}]_{80}$ A suspension of $(M_{0.2}K_{0.8})_{80}$ (6 mg) in a mixture of 0.1 M NaOAc/AcOH (0.17 mL) and HFIP (0.030 mL) was treated with 4a (1.5 μL, 2 eq per Met residue). The mixture was stirred vigorously for 16 h at RT. The mixture was treated again with 4a (1.5 μL, 2 eq per Met residue) and stirring was continued for another 24 h. The reaction mixture was transferred to a 2 kDa MWCO dialysis bag and dialyzed against 3 mM $HCl_{(aq)}$ (24 h, 3 $H_2O$ changes). The retentate was lyophilized, to provide 21 (6.2 mg, 88% yield). $^1$H NMR (400 MHz, $D_2O$, 25° C.): δ 4.68-4.57 (br m, 0.2H), 4.52-4.16 (br m, 1.2H), 3.88-3.35 (br m, 1.2H), 3.08 (m, 2.6H), 2.49-2.20 (br m, 0.4H), 2.16-1.24 (br m, 6H).

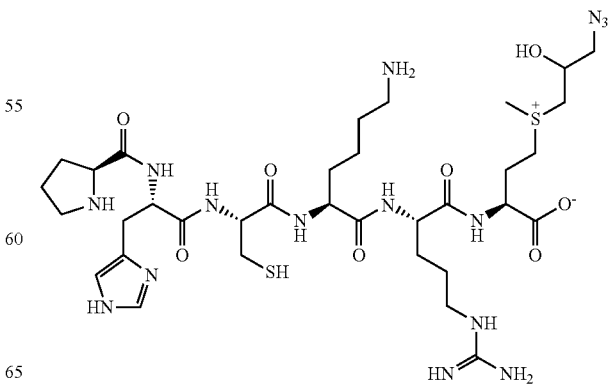

PHCKRM-Glycidyl Azide Conjugate, 18

A solution of peptide PHCKRM (2.0 mg, 0.0026 mmol) in glacial AcOH (0.30 mL) was treated with 4a (2.6 mg, 0.026 mmol). The solution was stirred for 48 h. The mixture was concentrated under high vacuum and the residue was triturated with 3×0.5 mL Et$_2$O; the solids were separated by centrifugation after each step. Residual ether was evaporated under high vacuum and completely removed by re-dissolving the solid in H$_2$O (0.5 mL) and lyophilizing the solution. Colorless solid (1.7 mg). ESI-MS m/z=870.1824 M$^+$ (calcd 870.4191 for $C_{34}H_{60}N_{15}O_8S_2$).

Example 5

Preparation of Epoxides

Epoxidation Procedure (Procedure D)

The alkene (1 eq) was dissolved in CH$_2$Cl$_2$ (3.3 mL/mmol alkene). Commercial 70% mCPBA (1.5 eq) was added and the mixture was stirred at room temperature. After TLC showed full conversion of the alkene (36-48 h) the suspension was cooled on an ice bath. The mixture was treated with 10% Na$_2$SO$_3$ $_{(aq)}$ (1.5 eq) followed by 10% Na$_2$CO$_3$ $_{(aq)}$ (1.3 eq) and stirred for 5 min. The reaction mixture was diluted with EtOAc, and washed 2× with sat. NaHCO$_3$ $_{(aq)}$ followed by brine. The organic extract were dried over Na$_2$SO$_4$, concentrated in vacuo and purified by flash chromatography.

'Dry' Epoxidation Procedure (Procedure E)

A stock solution of 0.45 M mCPBA in CH$_2$Cl$_2$ was prepared from commercial 70% mCPBA. This solution was dried over MgSO$_4$ and freed of drying agent by centrifugation. The alkene (1 eq) was treated with this 'dry' mCPBA solution (1.5 eq). Thereafter, the synthesis was conducted analogous to Procedure D.

Glycidyl azide, 4a

Epichlorohydrin (4.0 mL, 51 mmol) was added to a solution of sodium azide (4.0 g, 61 mmol) and acetic acid (3.5 mL, 61 mmol) in 25% (v/v) ethanol/water (20 mL). The biphasic mixture was stirred vigorously at room temperature for 24 h. Brine (25 mL) was added and the mixture was extracted with EtOAc (3×40 mL). The combined extracts were dried over Na$_2$SO$_4$ and concentrated in vacuo to provide 1-azido-3-chloropropan-2-ol as a colorless oil (6.7 g, 97% yield). $^1$H NMR (400 MHz, CDCl$_3$, 25° C.): δ 3.99 (pent, J=5.5 Hz, 1H), 3.66-3.56 (m, 2H), 3.48 (d, J=5.3 Hz, 2H).

An aqueous solution of 1 N sodium hydroxide (55 mL, 55 mmol) was added to 1-azido-3-chloropropan-2-ol with stirring on a RT H$_2$O bath. Stirring was continued for 30 min after the addition. The suspension was then extracted with CH$_2$Cl$_2$ (3×30 mL). The combined extracts were washed with brine (20 mL) and dried over Na$_2$SO$_4$. Concentration in vacuo provided 4a (4.0 g, 83% yield) as a colorless mobile oil. $^1$H NMR (400 MHz, CDCl$_3$, 25° C.): δ 3.56 (dd, J=13.8, 3.2 Hz, 1H), 3.31 (dd, J=13.5, 5.4 Hz, 1H), 3.19 (m, 1H), 2.84 (dd, J=4.7, 4.1 Hz, 1H), 2.71 (dd, J=4.8, 2.5 Hz, 1H).

2,2,2-trifluoro-N-(oxiran-2-ylmethyl)acetamide, 5a

Prepared from N-allyl-2,2,2-trifluoroacetamide by Procedure D. Flash chromatography eluent: 30% EtOAc/Hexanes. Colorless mobile oil, 74% yield. R$_F$: 0.33; 30% EtOAc/Hexanes. $^1$H NMR (300 MHz, CDCl$_3$, 25° C.): δ 7.35-6.99 (br s, 1H), 3.82 (ddd, J=14.7, 6.3, 3.0 Hz, 1H), 3.34 (dt, J=14.6, 5.7 Hz, 1H), 3.14 (m, 1H), 2.82 (t, J=4.3 Hz, 1H), 2.60 (dd, J=4.5, 2.8 Hz, 1H). $^{13}$C NMR (100 MHz, CDCl$_3$, 25° C.): δ 158.4 (q, J=37.8 Hz), 120.2 (q, J=287.4 Hz), 49.8, 45.3, 41.4. $^{19}$F NMR (376 MHz, D$_2$O, 25° C.): δ-76.0.

2-(2,5,8,11-tetraoxadodecyl)oxirane, 8a

A stirred solution of triethylene glycol monomethyl ether (10 g, 61 mmol) and water (1.0 mL) on an ice bath was treated with NaOH (7.2 g, 180 mmol) followed by 0.4 M tetrabutylammonium hydroxide$_{(aq)}$ (7.7 mL, 3.1 mmol). Once the mixture returned to 0° C., epichlorohydrin (14 mL, 180 mmol) was added portionwise over 3 min. The mixture was stirred at room temperature 16 h. H$_2$O (15 mL) was added and the mixture was extracted with EtOAc (4×30 mL). The combined extracts were washed with brine (30 mL) and dried over Na$_2$SO$_4$. The extracts were concentrated by rotary evaporation. The residue was distilled in vacuo, providing 8a (11 g, 79% yield) as a colorless liquid boiling at 110-117° C. (0.1 mmHg). $^1$H NMR (400 MHz, CDCl$_3$, 25° C.): δ 3.80 (dd, J=15.5, 4.1, 1H), 3.71-3.62 (m, 10H), 3.54 (m, 2H), 3.44 (dd, J=15.5, 7.8 Hz, 1H), 3.37 (s, 3H), 3.15 (m, 1H), 2.79 (dd, J=6.6, 5.6 Hz, 1H), 2.61 (dd, J=6.7, 3.6 Hz, 1 H).

Diisopropyl allylphosphonate, 9b

Allyl bromide (1.8 mL, 20 mmol) was added to a mixture of BHT (10 mg) in triisopropyl phosphite (5 mL, 20 mmol). The flask was set-up for reflux and heated on a 115° C. oil bath for 16 h. The reaction mixture was vacuum distilled to provide 9b (4.2 g, 100% yield) as a colorless oil boiling at 40-41° C. (0.1 mmHg). $^1$H NMR (400 MHz, CDCl$_3$, 25° C.): δ 5.83-5.75 (m, 1H), 5.18 (m, 2H), 4.72-4.64 (m, 2H), 2.58 (dd, J=21.9, 7.4 Hz, 2H), 1.30 (dd, J=6.2, 4.6 Hz, 12H).

Diisopropyl (oxiran-2-ylmethyl)phosphonate, 9a

Prepared from 9b by Procedure D. Flash chromatography eluent, 75% EtOAc/Hexanes to neat EtOAc. Colorless oil. Yield 75%. $R_F$: 0.2; 75% EtOAc/Hexanes. $^1$H NMR (400 MHz, CDCl$_3$, 25° C.): δ 4.74 (m, 2H), 3.17 (m, 1H), 2.84 (t, J=4.8 Hz, 1H), 2.59 (dd, J=4.8, 2.6 Hz, 1H), 2.22 (m, 1H), 1.77 (ddd, J=21.9, 15.0, 6.7 Hz, 1H), 1.34 (d, J=6.4 Hz, 12H).

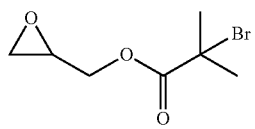

Glycidyl 2-bromo-2-methylpropanoate, 10a

Prepared by previously reported procedure. Gadwal, I.; Khan A. *Polym. Chem.* 2013, 4, 2440-2444.

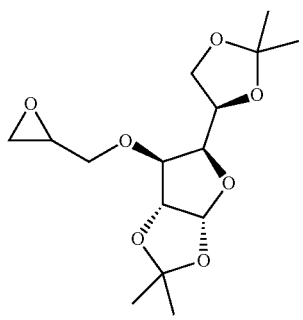 [SMILES: CC1(C)O[C@H]2O[C@H]([C@H]3COC(C)(C)O3)[C@H](OCC3CO3)[C@H]2O1]

2-((1,2:5,6-Di-O-isopropylidene-3-deoxy-α-D-glucofuranosid-3-yl)oxymethyl)oxirane, 11a Prepared by previously reported procedure. Khan, A. R; Tripathi, R. P.; Bhaduri, A. p.; Sahai, R.; Puri, A.; Tripathi, L. M.; Srivastava, V. M. L. *Eur. J. Med. Chem.* 2001, 36, 435-445.

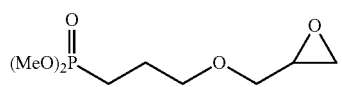

2-(3-(dimethoxyphosphoryl)propoxymethyl)oxirane, 12a

Prepared by previously reported procedure. Brel, A. K.; Petrov, V. I.; Ozerov, A. A.; Gunger, A. A.; Sazhin, V. A. *Pharm Chem J.* 1992, 26, 772-774.

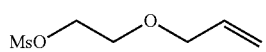

2-allyloxyethyl methanesulfonate

Prepared by previously reported procedure. Bala K.; Hailes H. C. *Synthesis* 2005, 2005, 3423-3427. Colorless to pale yellow oil, stable at room temp when stored in amber glass bottle.

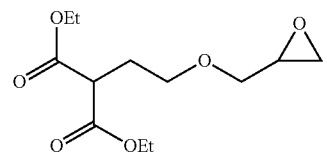 [SMILES: CCOC(=O)C(CCOCC1CO1)C(=O)OCC]

2-(2-(1,3-diethoxy-1,3-dioxopropan-2-yl)ethoxymethyl)oxirane, 13a

A suspension of 60% NaH (1.44 g, 36 mmol) and KI (5.4 g, 1 eq) in DMF (125 mL) was stirred on an ice bath. Diethyl malonate (5.0 mL, 33 mmol) was added dropwise and allowed to stir for 5 min. 2-Allyloxyethyl methanesulfonate (8.8 g, 49 mmol) was added portionwise. The mixture was stirred at 60° C. for 18 h. The solvent was evaporated in vacuo and the residue was diluted with 200 mL EtOAc. The solution was washed with 250 mL H$_2$O. The aqueous wash was extracted with 2×125 mL EtOAc. The combined organic extracts were dried over Na$_2$SO$_4$ and concentrated by rotary evaporation. The residue was purified by filtering through a silica plug with 10% EtOAc/Hexanes. After concentration, 7.3 g of a colorless oil was recovered. The oil was found by $^1$H NMR to contain diethyl 2-(2-(allyloxy)ethyl)malonate (79% yield) with 12 mol % diethyl 2,2-bis(2-(allyloxy)ethyl)malonate. From this mixture 13a was prepared by Procedure D. Flash chromatography eluent: 25% EtOAc/Hexanes. The title compound, 13a (6.5 g, 76% yield overall) was recovered as a colorless oil. $R_F$=0.39; 30% EtOAc/Hexanes. $^1$H NMR (400 MHz, CDCl$_3$, 25° C.): δ 4.19 (q, J=7.0 Hz, 4H), 3.70 (dd, J=11.8, 3.0 Hz, 1H), 3.53 (m, 3H), 3.35 (dd, J=11.8, 5.6 Hz, 1H), 3.10 (m, 1H), 2.77 (t, J=4.5 Hz, 1H), 2.58 (dd, J=5.0, 2.5 Hz, 1H), 2.18 (q, J=6.3 Hz, 2H), 1.26 (t, J=7.2 Hz, 6H). $^{13}$C NMR (100 MHz, CDCl$_3$, 25° C.): δ 169.2, 71.3, 68.5, 61.3, 50.6, 48.9, 44.0, 28.7, 13.9. ESI-MS m/z=283.2110 [M+Na]$^+$ (calcd 283.1158 for C$_{12}$H$_{20}$NaO$_6$).

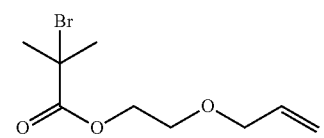

2-(allyloxy)ethyl 2-bromo-2-methylpropanoate, 14b

A solution of 2-allyloxyethanol (1.0 mL, 9.3 mmol) and pyridine (2.3 mL, 28 mmol) in CH$_2$Cl$_2$ (75 mL) was stirred on a −10° C. MeOH bath. 2-Bromoisobutyryl bromide (2.3 mL, 19 mmol) was added dropwise. The solution was removed from the bath and stirred at room temperature for 3.5 h. Water (0.3 mL) was added and the solution was concentrated in vacuo. The residue was purified by flash chromatography, 15% EtOAc/Hexanes. 12a was recovered as a colorless oil (2.2 g, 99%). $R_F$=0.50; 15% EtOAc/Hexanes. $^1$H NMR (400 MHz, CDCl$_3$, 25° C.): δ 5.87 (m, 1H), 5.31 (dm, J=17.3 Hz, 1H), 5.20 (dm, J=10.5 Hz, 1H), 4.33 (t, J=5.0 Hz, 2H), 4.03 (dt, J=5.6, 1.5 Hz, 2H), 3.69 (t, J=5.0 Hz, 2H), 1.94 (s, 6H). $^{13}$C NMR (100 MHz, CDCl$_3$, 25° C.): δ 171.6, 134.3, 117.2, 72.0, 67.4, 65.0, 55.6, 30.7. ESI-MS m/z=273.2030 [M+Na]$^+$ (calcd 273.0102 for C$_9$H$_{15}$BrO$_3$Na).

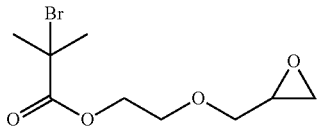

2-(2-((2-bromo-2-methylpropanoyl)oxy)ethanoxymethyl)oxirane, 14a

Prepared from 14b by Procedure D. Flash chromatography eluent: 30% EtOAc/Hexanes. Recovered as a colorless oil, 71% yield. R$_F$=0.34; 30% EtOAc/Hexanes. $^1$H NMR (400 MHz, CDCl$_3$, 25° C.): δ 4.33 (t, J=5.1 Hz, 2H), 3.73 (m, 3H), 3.46 (dd, J=11.7, 5.7 Hz, 1H), 3.16 (m, 1H), 2.77 (dd, J=5.0, 4.2 Hz, 1H), 2.62 (dd, J=5.1, 2.7 Hz), 1.94 (s, 6H). $^{13}$C NMR (100 MHz, CDCl$_3$, 25° C.): δ 171.5, 71.7, 68.8, 64.9, 55.6, 50.7, 43.9, 30.7. ESI-MS m/z=289.00 [M+Na]$^+$ (calcd 289.01 for C$_9$H$_{15}$BrO$_4$Na).

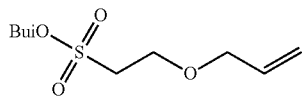

Isobutyl 2-(allyloxy)ethane-1-sulfonate, 15b

Isobutyl ethenesulfonate (0.50 mL, 3.6 mmol) was added to dry allyl alcohol (7.0 mL). The mixture was stirred on a MeOH bath maintained at ca. −20° C. by periodic additions of LN2. KOtBu (40 mg, 0.36 mmol) was added. The mixture was stirred overnight while the bath was allowed to warm to 10° C. AcOH (6 µL, 0.4 mmol) was added and the mixture was concentrated in vacuo. The residue was dissolved in EtOAc (50 mL) and washed with 0.01 N HCl$_{(aq)}$ (40 mL) followed by H$_2$O (40 mL). The organic extract was dried over Na$_2$SO$_4$ and concentrated by rotary evaporation. The residue was purified by flash chromatography (15% EtOAc/Hexanes). Alkene 15b (0.50 g, 62% yield) was recovered as a colorless oil. R$_F$=0.30; 15% EtOAc/Hexanes. $^1$H NMR (400 MHz, CDCl$_3$, 25° C.): δ 5.89 (m, 1H), 5.27 (dm, J=17.2 Hz, 1H), 5.21 (dm, J=10.5 Hz, 1H), 4.02 (dt, J=5.6, 1.4 Hz, 2H), 4.01 (d, J=6.6 Hz, 2H), 3.86 (t, J=6.4 Hz, 2H), 3.39 (t, J=6.6 Hz, 2H), 2.02 (sep, J=6.6 Hz, 1H), 0.98 (d, J=6.6 Hz, 6H). $^{13}$C NMR (100 MHz, CDCl$_3$, 25° C.): δ 133.8, 117.9, 76.1, 72.3, 63.6, 50.4, 28.3, 18.7. ESI-MS m/z=245.0810 [M+Na]$^+$ (calcd 245.0823 for C$_9$H$_{18}$O$_4$SNa).

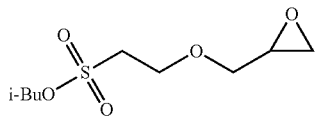

Isobutyl 2-(oxiran-2-ylmethoxy)ethane-1-sulfonate, 15a

Prepared from 15b by Procedure D. Flash chromatography eluent: 30% EtOAc/Hexanes. Recovered as a colorless oil, 78% yield. R$_F$=0.32; 40% EtOAc/Hexanes. $^1$H NMR (400 MHz, CDCl$_3$, 25° C.): δ 4.00 (d, J=6.6 Hz, 2H), 3.91 (m, 2H), 3.84 (dd, J=11.6, 2.6 Hz, 1H), 3.39 (d, J=6.6 Hz, 2 h), 3.37 (d, J=5.7 Hz, 1H), 3.13 (m, 1H), 2.78 (t, J=4.4 Hz, 1H), 2.60 (dd, J=4.8, 2.4 Hz, 1H), 2.01 (sep, J=6.6 Hz, 1H), 0.98 (d, J=6.8 Hz, 6H). $^{13}$C NMR (100 MHz, CDCl$_3$, 25° C.): δ 76.1, 72.0, 64.9, 50.5, 50.3, 44.0, 28.3, 18.6. ESI-MS m/z=245.0823 [M+Na]$^+$ (calcd 261.0773 for C$_9$H$_{18}$O$_5$SNa).

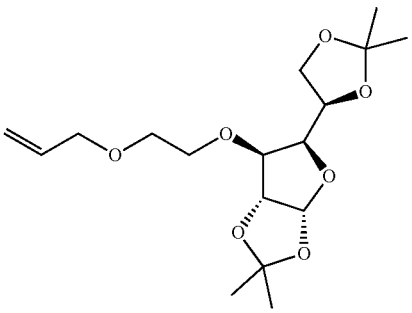 [SMILES: C=CCOCCO[C@@H]1[C@H]2OC(C)(C)O[C@H]2O[C@@H]1[C@H]1COC(C)(C)O1]

3-(2-(allyloxy)ethyloxy)1,2:5,6-di-O-isopropylidene-3-deoxy-α-D-glucofuranoside, 16b 1,2:5,6-di-O-isopropylidene-α-D-glucofuranose (0.75 g, 2.9 mmol) and KI (0.46 g, 2.9 mmol) were dried under high vacuum for ca. 15 min. DMF (40 mL) was transferred by cannula into the reaction flask, and the mixture was cooled on an ice bath. 60% NaH (0.17 g, 4.3 mmol) was added in one portion. After 5 min, the ice bath was removed and the mixture was allowed to stir 20 min at room temperature. 2-allyloxyethyl methanesulfonate (1.2 mL, 5.7 mmol) was added and the mixture was stirred 48 h on a 60° C. oil bath. The reaction mixture was concentrated under high vacuum overnight. The residue was directly purified by flash chromatography (7.5% Acetone/Hexanes). Alkene 16b (0.80 g, 81% yield) was recovered as a thick colorless oil. R$_F$=0.24; 10% Acetone/Hexanes. $^1$H NMR (400 MHz, CDCl$_3$, 25° C.): δ 5.89 (m, 2H), 5.29 (dm, J=17.3 Hz, 1H), 5.19 (dm, J=10.9 Hz, 1H), 4.59 (d, J=4.1 Hz, 1H), 4.32 (q, J=6.12, 1H), 4.12 (dd, J=7.5, 3.0 Hz, 1H), 4.08 (dd, J=8.5, 6.1 Hz, 1H), 4.00 (m, 3H), 3.93 (d, J=2.7 Hz, 1H), 3.75 (m, 2H), 3.56 (t, J=4.8 Hz, 2H), 1.49 (s, 3H), 1.42 (s, 3H), 1.34 (s, 3H), 1.30 (s, 3H). $^{13}$C NMR (100 MHz, CDCl$_3$, 25° C.): δ 134.6, 116.8, 111.6, 108.8, 105.2, 82.7, 82.6, 81.1, 72.5, 72.1, 70.2, 69.3, 67.1, 26.8, 26.7, 26.1, 25.3. ESI-MS m/z=367.18 [M+Na]$^+$ (calcd 367.17 for C$_{17}$H$_{28}$O$_7$Na).

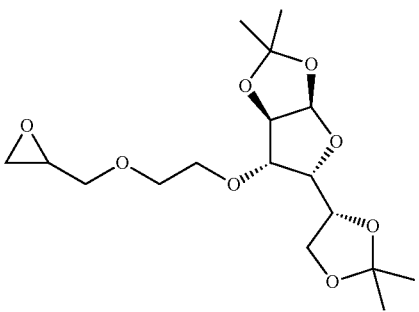 [SMILES: CC1(C)O[C@H]2O[C@H]([C@H]3COC(C)(C)O3)[C@H](OCCOCC3CO3)[C@H]2O1]

2-(2-((1,2:5,6-di-O-isopropylidene-3-deoxy-α-D-glucofuranosid-3-yl)oxy)ethoxymethyl)oxirane, 16a Prepared from 16b by Procedure E. Flash chromatography eluent: 20% Acetone/Hexanes. Colorless thick oil, 82% yield. $R_F$=0.30; 20% Acetone/Hexanes. $^1$H NMR (400 MHz, CDCl$_3$, 25° C.): δ 5.87 (d, J=3.8 Hz, 1H), 4.57 (d, J=3.5 Hz, 1H), 4.32 (q, J=6.2 Hz, 1H), 4.10 (m, 2H), 3.99 (dd, J=8.5, 5.8 Hz, 1H), 3.93 (d, J=2.8 Hz, 1H), 3.80 (dd, J=11.7, 2.8 Hz, 1H), 3.77-3.63 (m, 4H), 3.41 (ddd, J=11.3, 5.8, 3.5 Hz, 1H), 3.14 (m, 1H), 2.78 (t, J=4.6 Hz, 1H), 2.60 (m, 1 H), 1.48 (s, 3H), 1.41 (s, 3H), 1.33 (s, 3H), 1.31 (s, 3H). $^{13}$C NMR (100 MHz, CDCl$_3$, 25° C.): δ 111.6, 108.8, 105.2, 82.7, 82.6, 81.0, 72.4, 71.8, 70.6, 70.0, 67.1, 50.7, 44.0, 26.8, 26.7, 26.1, 25.3. ESI-MS m/z=383.1663 [M+Na]$^+$ (calcd 383.1682 for C$_{17}$H$_{28}$O$_8$Na).

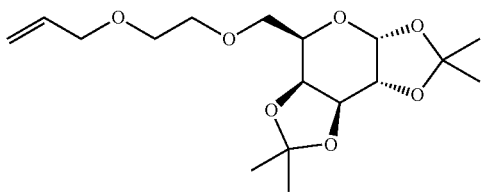 [SMILES: C=CCOCCOC[C@H]1O[C@@H]2OC(C)(C)O[C@@H]2[C@H]2OC(C)(C)O[C@H]21]

6-(2-(allyloxy)ethyloxy)-1,2:3,4-dDi-O-isopropylidene-6-deoxy-α-D-galactopyranoside, 17b Prepared analogously to 16b using 1,2:3,4-di-O-isopropylidene-α-D-galactopyranose as the substrate. Flash chromatography eluent: 7.5% Acetone/Hexanes. Colorless thick oil, 86% yield. $R_F$=0.31; 10% Acetone/Hexanes. $^1$H NMR (400 MHz, CDCl$_3$, 25° C.): δ 5.94 (m, 1H), 5.54 (d, J=5.0 Hz, 1H), 5.30 (dq, J=16.9, 1.5 Hz, 1H), 5.19 (dm, J=10.7 Hz, 1H), 4.61 (dd, J=8.0, 2.4 Hz, 1H), 4.31 (dd, J=5.0, 2.4 Hz, 1H), 4.28 (dd, J=7.7, 2.1 Hz, 1H), 4.03 (m, 3H), 3.75-3.60 (m, 6H), 1.53 (s, 3H), 1.44 (s, 3H), 1.34 (s, 3H), 1.33 (s, 3H). $^{13}$C NMR (100 MHz, CDCl$_3$, 25° C.): δ 134.8, 116.9, 109.1, 108.4, 96.3, 72.1, 71.1, 70.7, 70.6, 70.5, 69.8, 69.3, 66.7, 26.0, 25.9, 24.8, 24.3. ESI-MS m/z=367.17 [M+Na]$^+$ (calcd 367.17 for C$_{17}$H$_{28}$O$_7$Na).

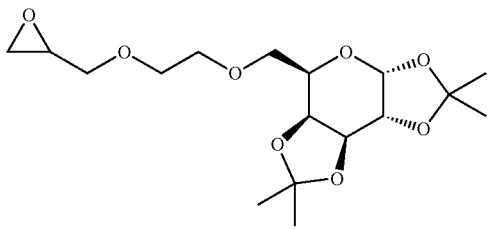 [SMILES: CC1(C)O[C@H]2[C@@H](O1)[C@@H](COCCOCC1CO1)O[C@@H]1OC(C)(C)O[C@@H]12]

2-(2-((1,2:3,4-di-O-isopropylidene-6-deoxy-α-D-galactopyranosid-6-yl)oxy)ethoxymethyl)oxirane, 17a Prepared from 17b by Procedure E. Flash chromatography eluent: 15-20% Acetone/Hexanes. Colorless thick oil, 94% yield. $R_F$=0.19; 15% Acetone/Hexanes. $^1$H NMR (400 MHz, CDCl$_3$, 25° C.): δ 5.53 (d, J=5.0 Hz, 1H), 4.60 (dd, J=8.1, 2.5 Hz, 1H), 4.30 (dd, J=4.9, 2.4 Hz, 1H), 4.26 (dd, J=7.9, 1.5 Hz, 1H), 3.98 (t, J=6.1 Hz, 1H), 3.79 (dm, J=11.7 Hz), 3.72-3.60 (m, 6H), 3.47 (ddd, J=11.6, 5.7, 3.3 Hz, 1H), 3.15 (m, 1H), 2.78 (t, J=4.7 Hz, 1H), 2.61 (m, 1H), 1.53 (s, 3H), 1.43 (s, 3H), 1.33 (s, 3H), 1.32 (s, 3H). $^{13}$C NMR (100 MHz, CDCl$_3$, 25° C.): δ 109.3, 108.6, 96.4, 72.0, 71.9, 71.2, 70.9, 70.7, 70.6, 70.0, 66.9, 50.9, 44.4, 26.2, 26.1, 25.0, 24.5. ESI-MS m/z=383.1698 [M+Na]$^+$ (calcd 383.1682 for C$_{17}$H$_{28}$O$_8$Na).

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of Formula I:

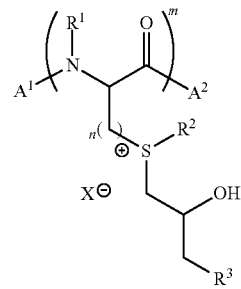

Formula I wherein, independently for each occurrence,
   $R^1$ is H or alkyl;
   $R^2$ is alkyl;
   $R^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido;
   m is 1-200, inclusive;
   n is 1-4, inclusive;
   $A^1$ is H, an amine protecting group, a natural or unnatural alpha amino acid, a peptide, an oligopeptide, a polypeptide, or a protein;
   $A^2$ is OH, —O-(a carboxylate protecting group), a natural or unnatural alpha amino acid, a peptide, an oligopeptide, a polypeptide, or a protein; and
   X is a monovalent anion.

2. The compound of claim 1, wherein $R^3$ is substituted alkyloxy.

3. The compound of claim 2, wherein $R^3$ is heterocycloalkyloxy, phosphonate-substituted alkyloxy, acyloxyalkyloxy, aminoalkyloxy, aminoalkylamidoalkyloxy, or alkyloxycarbonylalkyloxy.

4. The compound of claim 1, wherein $R^3$ is -L-halo, -L-azide, -L-NHR$^1$, -L-NR$^1$-TFA, -L-NR$^1$—C(O)—O-alkyl, -L-NR$^1$—C(O)—CH$_2$—NR$^1$-TFA, -L-O—CH$_2$—CH=CH$_2$, -L-O—CH$_2$CCH, -L-O-alkyl, -L-O—C(O)-alkyl, -L-P(O)(O-alkyl)$_2$, -L-P(O)(OH)$_2$, -L-O—C(O)—C(halo)(alkyl)$_2$, -L-CH$_2$—P(O)(O-alkyl)$_2$, -L-CH$_2$—P(O)(OH)$_2$, -L-O—CH$_2$CH—(C(O)NR$^1$-alkyl)(NR$^1$-TFA), -L-O—CH$_2$CH—(C(O)OR$^1$)(NR$^1$-TFA), -L-OCH$_2$—C (O)—OR$^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

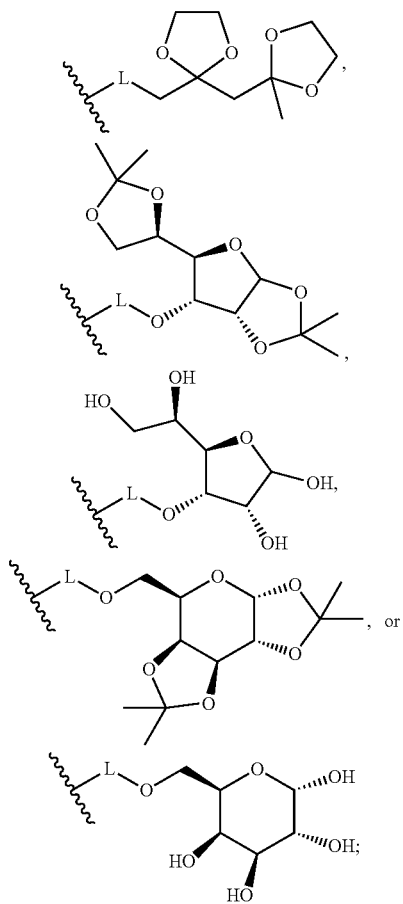

L is a bond or —(OCH$_2$CH$_2$)$_x$—, and x is 1-10.

5. The compound of claim 1, wherein A$^1$ or A$^2$ is methionine, or A$^1$ or A$^2$ is a peptide comprising a methionine residue, an oligopeptide comprising a methionine residue, a polypeptide comprising a methionine residue, or a protein comprising a methionine residue.

6. The compound of claim 1, wherein A$^1$ or A$^2$ is cysteine, or A$^1$ or A$^2$ is a peptide comprising a cysteine residue, an oligopeptide comprising a cysteine residue, a polypeptide comprising a cysteine residue, or a protein comprising a cysteine residue.

7. A peptide, an oligopeptide, a polypeptide, or a protein, wherein the peptide, oligopeptide, polypeptide, or protein comprises substructure I Substructure I

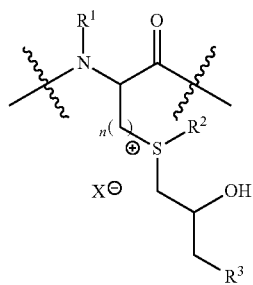

wherein,

R$^1$ is H or alkyl;

R$^2$ is alkyl;

R$^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido;

n is 1-4, inclusive; and

X is a monovalent anion.

8. The peptide, oligopeptide, polypeptide, or protein of claim 7, wherein the peptide, oligopeptide, polypeptide, or protein comprises a plurality of substructures I.

9. The peptide, oligopeptide, polypeptide, or protein of claim 7, wherein R$^3$ is substituted alkyloxy.

10. The peptide, oligopeptide, polypeptide, or protein of claim 9, wherein R$^3$ is heterocycloalkyloxy, phosphonate-substituted alkyloxy, acyloxyalkyloxy, aminoalkyloxy, aminoalkylamidoalkyloxy, or alkyloxycarbonylalkyloxy.

11. The peptide, oligopeptide, polypeptide, or protein of claim 7, wherein R$^3$ is -L-halo, -L-azide, -L-NHR$^1$, -L-NR$^1$-TFA,-L-NR$^1$—C(O)—O-alkyl -L-NR$^1$—C(O)—CH$_2$—NR$^1$-TFA, -L-O—CH$_2$—CH=CH$_2$, -L-O—CH$_2$CCH, -L-O-alkyl, -L-O—C(O)-alkyl, -L-P(O)(O-alkyl)$_2$, -L-P(O)(OH)$_2$, -L-O—C(O)—C(halo)(alkyl)$_2$, -L-CH$_2$—P(O)(O-alkyl)$_2$, -L-CH$_2$—P(O)(OH)$_2$, -L-O—CH$_2$CH—(C(O)NR$^1$-alkyl)(NR$^1$-TFA), -L-O—CH$_2$CH—(C(O)OR$^1$)(NR$^1$-TFA) , -L-OCH$_2$—C(O)—OR$^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

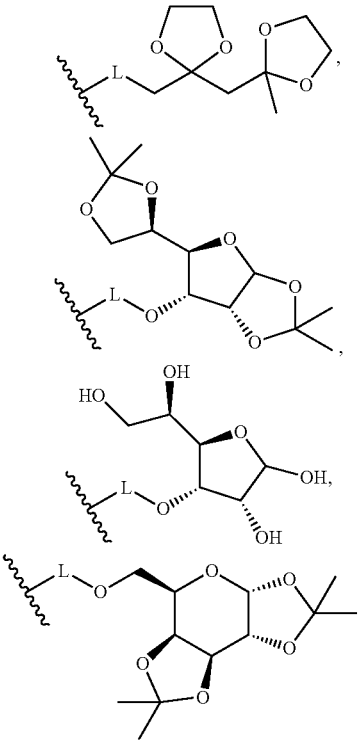

-continued

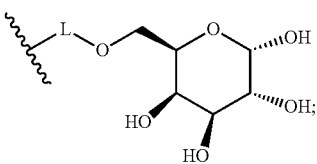

L is a bond or —(OCH$_2$CH$_2$)$_x$—, and x is 1-10.

12. The peptide, oligopeptide, polypeptide, or protein of claim 7, wherein R$^3$ is —(OCH$_2$CH$_2$)$_3$—OCH$_3$.

13. The peptide, oligopeptide, polypeptide, or protein of claim 7, wherein R$^3$ is

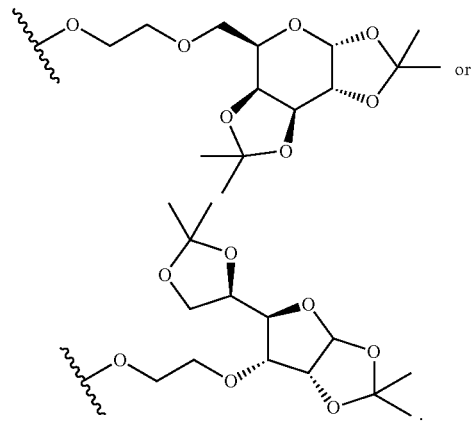

or

14. A process for chemically modifying a peptide, oligopeptide, polypeptide, or protein by alkylation of one or more thioether groups, comprising the steps of:

contacting a compound of formula II with an aqueous or polar organic solvent

Formula II

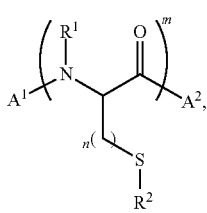

wherein, independently for each occurrence,

R$^1$ is H or alkyl;

R$^2$ is alkyl;

m is 1-200, inclusive;

n is 1-4, inclusive;

A$^1$ is H, an amine protecting group, a natural or unnatural alpha amino acid, a peptide, an oligopeptide, a polypeptide, or a protein;

A$^2$ is OH, —O-(a carboxylate protecting group), a natural or unnatural alpha amino acid, a peptide, an oligopeptide, a polypeptide, or a protein;

adding a compound of formula III

Formula III

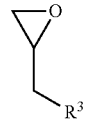

wherein, independently for each occurrence,

R$^3$ is H or substituted or unsubstituted amino, substituted or unsubstituted alkyl, substituted or unsubstituted alkyloxy, azido, substituted or unsubstituted aryl, substituted or unsubstituted heteroaryl, halo, substituted or unsubstituted allyloxy, substituted or unsubstituted alkylcarbonyloxy, substituted or unsubstituted phosphonate, substituted or unsubstituted carbamate, or substituted or unsubstituted amido; and reacting the compound of formula II with the compound of formula III, thereby creating a compound of formula I Formula I

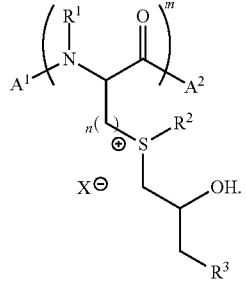

15. The process of claim 14, wherein R$^3$ is substituted alkyloxy.

16. The process of claim 15, wherein R$^3$ is heterocycloalkyloxy, phosphonate-substituted alkyloxy, acyloxyalkyloxy, aminoalkyloxy, aminoalkylamidoalkyloxy, or alkyloxycarbonylalkyloxy.

17. The process of claim 14, wherein R$^3$ is -L-halo, -L-azide, -L-NHR$^1$, -L-NR$^1$TFA, -L-NR$^1$—C(O)—O-alkyl, -L-NR$^1$—C(O)—CH$_2$—NR$^1$-TFA, -L-O—CH$_2$—CH=CH$_2$, -L-O—CH$_2$CCH, -L-O-alkyl, -L-O—C(O)-alkyl, -L-P(O)(O-alkyl)$_2$, -L-P(O)(OH)$_2$, -L-O—C(O)—C(halo)(alkyl)$_2$, -L-CH$_2$—P(O)(O-alkyl)$_2$, -L-CH$_2$—P(O)(OH)$_2$, -L-O—CH$_2$CH—(C(O)NR$^1$-alkyl)(NR$^1$-TFA), -L-O—CH$_2$CH—(C(O)OR$^1$)(NR$^1$-TFA), -L-OCH$_2$—C(O)—OR$^1$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

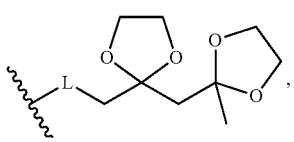

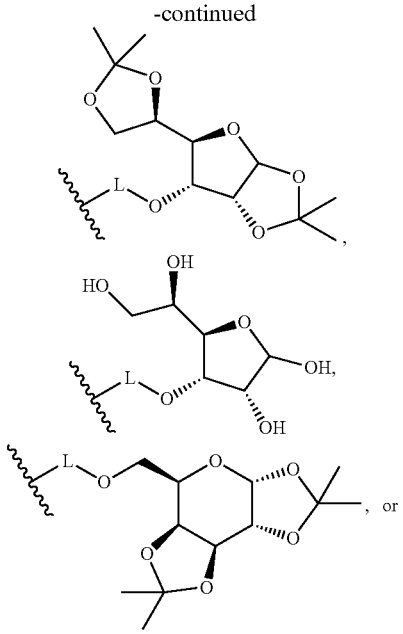

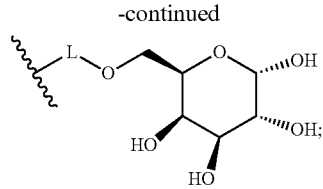

L is a bond or —(OCH$_2$CH$_2$)$_x$—, and x is 1-10.

18. The process of claim 14, wherein A$^1$ or A$^2$ is methionine, or A$^1$ or A$^2$ is a peptide comprising a methionine residue, an oligopeptide comprising a methionine residue, a polypeptide comprising a methionine residue, or a protein comprising a methionine residue.

19. The process of claim 14, wherein A$^1$ or A$^2$ is cysteine, or A$^1$ or A$^2$ is a peptide comprising a cysteine residue, an oligopeptide comprising a cysteine residue, a polypeptide comprising a cysteine residue, or a protein comprising a cysteine residue.

* * * * *